US012721863B2

(12) United States Patent
Kent et al.

(10) Patent No.: US 12,721,863 B2
(45) Date of Patent: Sep. 1, 2026

(54) TREATMENT FOR DOWN SYNDROME-RELATED ACCELERATED AGING

(71) Applicants: The Texas A&M University System, College Station, TX (US); The Trustees of Indiana University, Bloomington, IN (US)

(72) Inventors: Thomas A Kent, Houston, TX (US); Paul J. Derry, Houston, TX (US); Kenneth R. Olson, Berrien Springs, MI (US)

(73) Assignees: The Texas A&M University System, College Station, TX (US); The Trustees of Indiana University, Bloomington, IN (US)

( * ) Notice: Subject to any disclaimer, the term of this patent is extended or adjusted under 35 U.S.C. 154(b) by 115 days.

(21) Appl. No.: 18/567,972

(22) PCT Filed: Jun. 8, 2022

(86) PCT No.: PCT/US2022/032638
§ 371 (c)(1),
(2) Date: Dec. 7, 2023

(87) PCT Pub. No.: WO2022/261182
PCT Pub. Date: Dec. 15, 2022

(65) Prior Publication Data

US 2024/0269163 A1 Aug. 15, 2024

Related U.S. Application Data

(60) Provisional application No. 63/209,050, filed on Jun. 10, 2021.

(51) Int. Cl.

| | |
|---|---|
| ***A61K 31/765*** | (2006.01) |
| ***A61K 9/00*** | (2006.01) |
| ***A61K 31/385*** | (2006.01) |
| ***A61K 47/69*** | (2017.01) |
| ***A61P 43/00*** | (2006.01) |

(52) U.S. Cl.
CPC .......... *A61K 31/765* (2013.01); *A61K 9/0053* (2013.01); *A61K 31/385* (2013.01); *A61K 47/6921* (2017.08); *A61P 43/00* (2018.01)

(58) Field of Classification Search
None
See application file for complete search history.

(56) References Cited

FOREIGN PATENT DOCUMENTS

WO 2010072807 A2 7/2010

OTHER PUBLICATIONS

Extended European Search Report re application No. EP 22820946.6, dated Nov. 5, 2024. (9 pages).
Kamoun, P. et al. "Metal Retardation in Down Syndrome: Two Ways to Treat," Med Hypotheses, 131, 2019, 109289. doi: 10.1016/j.mehy.2019.109289. Epub Jun. 26, 2019. PMID: 31443780.
Wu, G. et al., "Oxidized Activated Charcoal Nanoparticles as Catalytic Superoxide Dismutase Mimetics: Evidence for Direct Participation of an Intrinsic Radical," ACS Applied Nano Materials 2020, 3 (7), 6962-6971. doi: 10.1021/acsanm.0c01285.
Panagaki, T. et al., "Overproduction of H2S, Generated by CBS, Inhibits Mitochondrial Complex IV and Suppresses Oxidative Phosphorylation in Down Syndrome," PNAS, Sep. 17, 2019, vol. 116, No. 38, pp. 18769-18771; https://www.pnas.org/cgi/doi/10.1073/pnas.1911895116.
Olson, K.R. et al., "Hydrogen Sulfide, Reactive Sulfur Species and Coping with Reactive Oxygen Species," Free Radical Biology and Medicine, 140 (2019) pp. 74-83; https://doi.org/10.1016/j.freeradbiomed.2019.01.020.
Olson, K.R. et al., "Are the Beneficial Effects of 'antioxidant' lipoic acid Mediated Through Metabolism of Reactive Sulfur Species?" Free Radical Biology and Medicine, 146 (2020) pp. 139-149; https://doi.org/10.1016/j.freeradbiomed.2019.10.410.
Derry, P.J. et al., "Catalytic Oxidation and Reduction Reactions of Hydrophilic Carbon Clusters with NADH and Cytochrome C: Features of an Electron Transport Nanozyme," Nanoscale, 2019, 11, pp. 10791-10807; doi: 10.1039/c9nr00807a.

*Primary Examiner* — Brian J Davis
(74) *Attorney, Agent, or Firm* — Meunier Carlin & Curfman LLC

(57) ABSTRACT

A method of treating a Down syndrome (DS) subject with functional or at risk of decline of organ systems associated with accelerated aging due to over-production of $H_2S$ is disclosed. That method contemplates administering a pharmaceutical composition containing a $H_2S$-reducing effective amount of hydrophilic polymer-substituted oxidized carbon nanoparticles (OCNPs) and an optional potentiating amount of lipoic acid or dihydrolipoic acid dissolved or dispersed in a physiologically acceptable diluent to the subject. The pharmaceutical composition can be administered parenterally as a liquid or per os as a solid or liquid.

24 Claims, 24 Drawing Sheets

PRIOR ART

Fig. 4
Fig. 4A
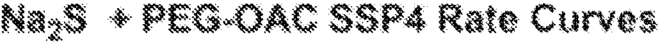
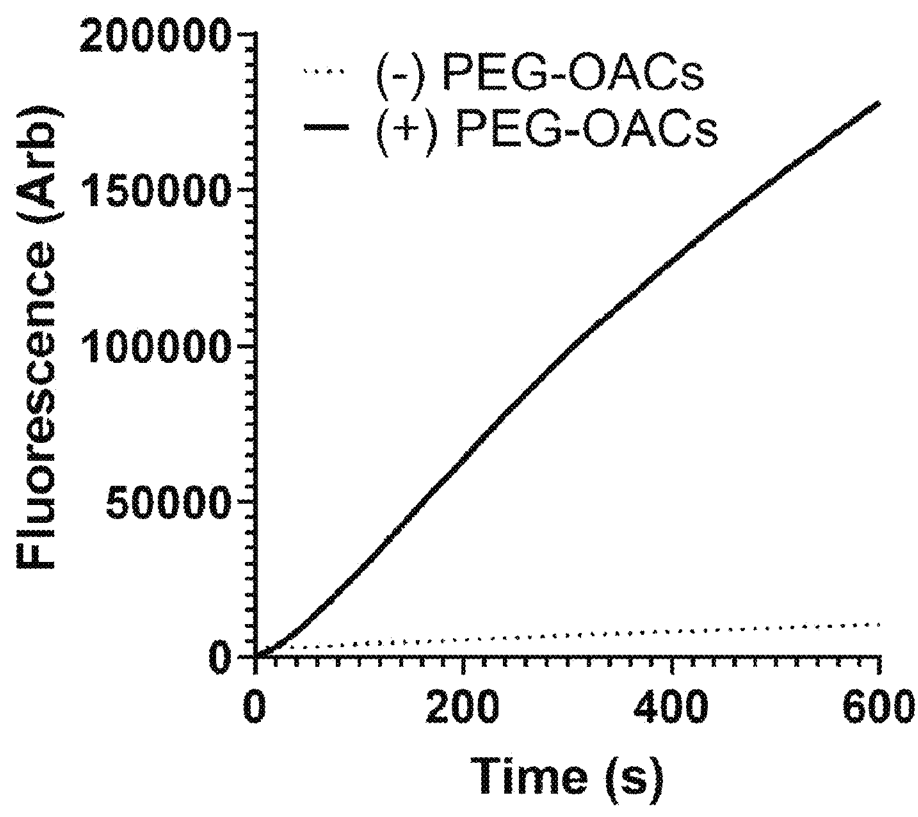

90% $HNO_3$
100 °C
6 h,
4 h (sieved)

OAC $H_2N$–(CH₂CH₂O)$_n$–$CH_3$
DIC, DMF
48 h

PEG-OAC

GM01920
Cells/mL (x10000)
600
450
300
150
0
0
2
4
6
8
Time (days)
GM001920 PBS
GM001920 NPs GM06993
Cells/mL (x10000)
600
450
300
150
0
0
2
4
6
8
Time (days)
GM06993 PBS
GM06993 NPs

Fig. 12
Fig. 12A
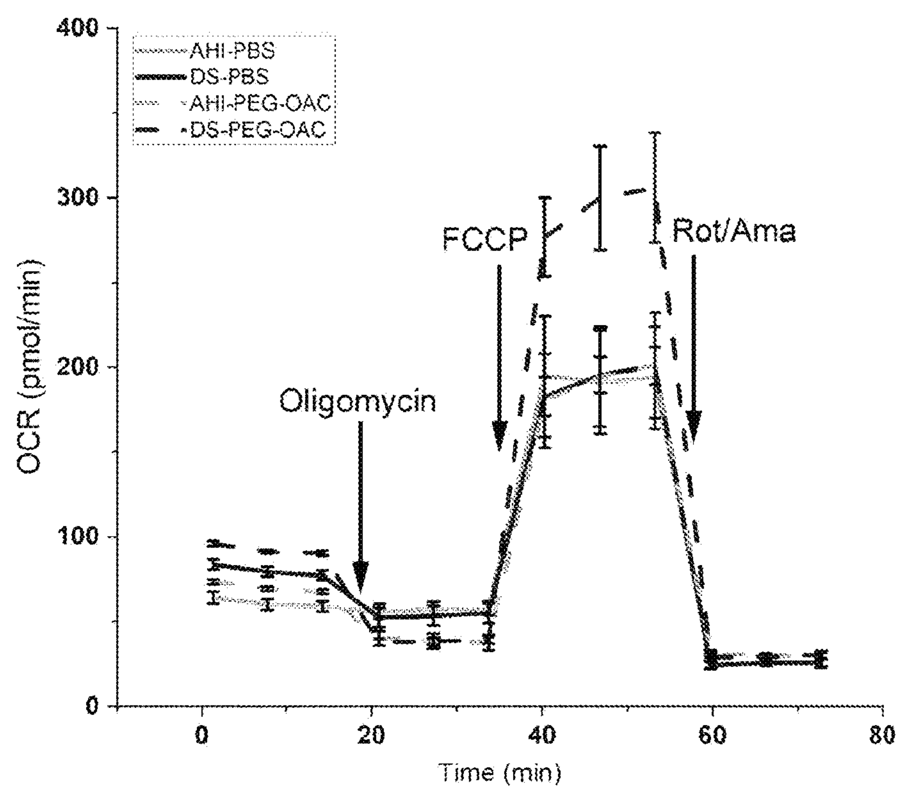
Fig. 12B
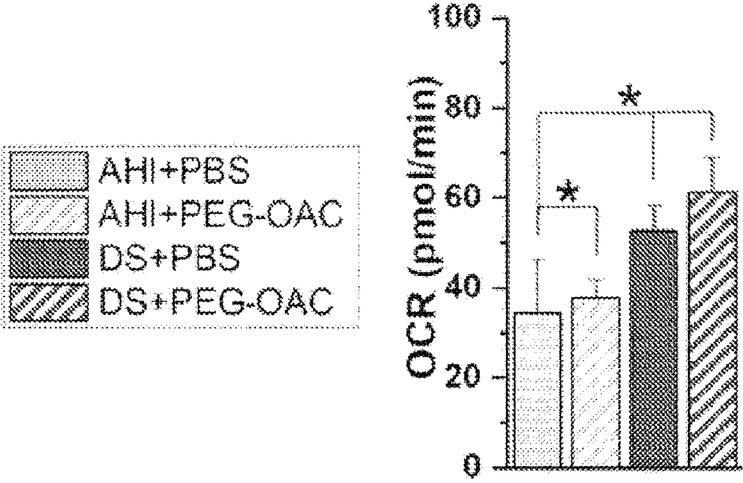

TREATMENT FOR DOWN SYNDROME-RELATED ACCELERATED AGING

STATEMENT OF GOVERNMENT LICENSE RIGHTS

This invention was made with government support under grant number R01NS094535 awarded by the National Institutes of Health and grant number IOS2012106 awarded by the National Science Foundation. The government has certain rights in the invention. This invention was also made with the support of the Welch Foundation under grant number BE-0048.

FIELD OF THE INVENTION

The present invention relates to the field of carbon nanomaterials and to their therapeutic uses in treating Down Syndrome-related accelerated aging.

BACKGROUND ART

Down Syndrome (DS) is a lifelong chronic disease with an increasing incidence rate and improving lifespans but without treatments for decline in multiple organ systems that occur prematurely in DS. DS is a genetic disease resulting from 3 copies (trisomy) of chromosome 21 that is actively transcribed. Carried on this chromosome are cystathionine-β-synthase (CBS) and amyloid precursor protein (APP), a protein associated with AD, among many others (1). Individuals with DS experience a plethora of common abnormalities including mental impairment, congenital heart defects, craniofacial abnormalities, hypotonia, and low bone mass leading to an increased risk of fractures (2, 3). DS is the most prevalent genetic disorder in the United States and life expectancies have increased over time, therefore it is imperative that new drugs be developed to improve the quality of life for individuals with this disease.

In the United States, the estimated incidence of DS as of 2008 is 1:700 livebirths or approximately 6,000 babies per year (4). The incidence of new DS cases has increased 30% between 1979 and 2003 and is positively correlated to average maternal age, which in the United States has increased over time (5). Additionally, DS prevalence is not distributed evenly among races with Black and Hispanic babies being most likely to have DS (4).

Those with DS can expect an increasingly long-life expectancy. In 1960 the average death age of a child with DS was approximately 10 years and is approximately 50 as of 2010. With increasing longevity, comes the effects of DS-associated accelerating aging (6, 7), which affects many organ systems such as weakening the immune system, accelerated osteoporosis and bone fractures, muscle mass decline and cognitive decline such as Alzheimer Disorder (DS-AD).

AD may be due in part to a transcribed third copy of amyloid precursor protein on Chromosome 21 (8). Virtually all individuals with DS carry sufficient amyloid plaque and neurofibrillary tangles for diagnosable AD (9) over the age of 40. It is hypothesized that excess $H_2S$ is involved in the disease process of DS, and potentially AD as well with evidence that CBS is overexpressed in the brain (10) and mitochondrial impairment in DS over time leads to the accumulation of amyloid plaque (11), one of the pathologies seen in AD.

Down Syndrome has characteristics of a metabolic disorder with a dysregulation of hydrogen sulfide that contributes to oxidative stress. The overexpression of CBS in DS has been reported extensively (12, 13) with Ichinohe et al. reporting a 3-fold excess (2). CBS belongs to the transsulfuration pathway, a direct offshoot of the folate and methionine cycles and initiates generation of cysteine from homocysteine among other roles (FIG. 1). Dysregulation of $H_2S$ has been associated with many of the features of decline in function, genomic instability and other features associated with aging.

The overexpression of CBS in DS increases endogenous production of $H_2S$ (14). Moreover, CBS has been shown to become activated by its own product, $H_2S$, thus creating a vicious cycle (15) of $H_2S$ production. Thus, conversion of $H_2S$ to polysulfides and thiosulfate can reduce CBS hyperactivity and provide beneficial polysulfides products. $H_2S$ tightly binds to the oxygen-reducing copper complexes of mitochondrial Complex IV (ferrocytochrome C:dioxygen oxidoreductase) and prevents the reduction of dioxygen to water and production of ATP (16). Inhibition of Complex IV blocks the electron transport chain (ETC) and leads to electrons from Complexes I and III being captured by dioxygen ($O_2$) forming ROS and damaging lipid peroxides (LOOH) (17) (FIG. 1).

Hydrogen sulfide ($H_2S$) is a gaseous transmitter carries out several critical biological functions but is toxic in excess. High levels of $H_2S$ are associated with numerous disease processes including Down Syndrome (DS; Trisomy 21) (16). The gene for cystathionine-β-synthase (CBS), a major producer of $H_2S$, is found on chromosome 21 and is also transcribed from the duplicated chromosome 21 (10). DS is a condition with no effective or approved therapy (18).

Although the characteristic facies and cognitive changes are well known, less well known is that there is functional decline in many DS individuals in many organ systems in that they experience many of the features of aging but at an earlier age, affecting overall function described as "slowing down", and function of the immune system, musculoskeletal system, gastrointestinal system, cardiac function as well as neurological function deteriorates over time and many patients will go on to display early aging features including in some changes characteristic of Alzheimer Disease (AD) (9, 17, 19). One possible reason for this deterioration is that excess $H_2S$ interferes with oxidative phosphorylation and signaling pathways including the brain (16) and metabolic abnormalities in muscle, bone, and other organ systems subject to this accelerated aging phenomenon.

The present invention contemplates a new approach to treating this decline by employing oxidized carbon nanoparticles (OCNPs) derived from medicinal grade activated charcoal, poly(ethylene glycol)-functionalized oxidized activated charcoal (PEG-OAC), that catalytically dismutate superoxide and shuttle electrons between mitochondrial constituents (20, WO 2021/252382).

We recently discovered that PEG-OACs also catalytically oxidize $H_2S$ into beneficial polysulfides. Converting $H_2S$ to polysulfide has beneficial effects because polysulfides quench reactive oxygen species (ROS) (23), promote critical persulfidation reactions (19), and reduce disulfides back to thiols (24). After quenching the ROS, polysulfides are converted to benign thiosulfate ($S_2O_3^{2-}$) that is excreted (25).

Channeling excess $H_2S$ into polysulfides and thiosulfate is an attractive therapeutic method to protect mitochondria and preserve function in DS and other conditions involving excess $H_2S$. Most proposed approaches involve scavenging or inhibiting $H_2S$ production, which is fraught with difficulty because although $H_2S$ has little actions on its own, some level is needed to generate these active metabolites, and in the case of $H_2S$, those enzymes are linked to the production of glutathione, a major endogenous antioxidant. OCNPs can reduce ROS load and restore the metabolic imbalance caused by an excess of CBS and $H_2S$.

Notably, there is considerable phenotypic variability in DS, and the biochemical underpinning of this heterogeneity is not fully understood. DS individuals have variability both at birth as well as decline in their clinical status. This decline includes musculoskeletal events such as hypotonia, early osteoporosis, fractures, cognition and other features that have been subsumed under the rubric of "accelerated aging" (26).

Lipid peroxidation is another important endpoint and a consequence of free radical formation by oxidative stress. Lipid peroxidation can be measured using the malondialdehyde (MDA) or thiobarbituric acid reactive derivatives (TBARS) assay, mass spectrometry, or fluorescence microscopy imaging using labels such as C11-BODIPY. Urinary thiosulfate levels can be measurable using a silver-tannic acid nanoparticle conjugate (30). Cysteine, cystine, glutathione, glutathione disulfide, methyl-folate, and homocysteine levels are also additional endpoints as these feed into and out of transsulfuration. The preferred method of quantitation is high performance liquid chromatography with electrospray mass spectrometry (ESI-MS).

Endogenous $H_2S$ is produced primarily through the transsulfuration pathway by cystathionine-β-synthase (CBS) and cystathionine-γ-lyase (CSE) (13). The roles of $H_2S$ in the body are varied, however a dysregulated excess is universally detrimental (14). In mitochondria, excess $H_2S$ impairs Complex IV which causes electron leakage due to the inability for oxygen to capture electrons from upstream Complexes (15). Inhibition of the electron transport chain (ETC) leads to an increased dependence on glycolysis (1) and reduction in ATP production.

Triplication of chromosome 21 also downregulates transcription of antioxidant response element (ARE)-dependent enzymes (34): NADPH:Quinone oxidoreductase (NQO1), heme oxygenase 1 (HO-1), glutamate-cysteine ligase regulatory and catalytic subunits (GCLC, GCLM) (34), Sulfiredoxin 1 (SRXN1), thioredoxin reductase (TXNRD1) (34), glutathione-S-transferase (GST), UDP-glucuronosyltransferase (UGT) (35), and potentially multidrug resistance-associated proteins (Mrps) (36). The collection of enzymes are largely for Phase II metabolism of electrophiles (37).

HO-1 begins the process of degrading reactive heme molecules that can generate reactive oxygen species. Glutathione and glucuronidation by UGT reduce circulation time by producing a water-soluble product which are removed from the cell by Mrps which increase the efflux of these new quenched products (36). NQO1 reduces the electrophile to eliminate electrophilic sites on the molecule. The last group, SRXN1 and TXNRD1, are highly potent catalysts that eliminate $H_2O_2$ and peroxynitrite (38, 39). With the loss of these enzymes, the antioxidant capacity of the cell is reduced and makes cells more prone to toxic insult by xenobiotics and peroxides.

ARE-dependent enzymes are expressed through the binding of the nuclear factor erythroid 2-related factor 2 (Nrf2) to the ARE sequences in nuclear DNA. Cells regulate the activity of Nrf2 through the protein Kelch-like ECH-associated protein (Keap1). Nrf2 and Keap1 form a complex that negatively regulates the activity of Nrf2 by promoting the proteosomic degradation of Nrf2.

Keap1 is a redox sensitive protein that is conformationally controlled by the oxidation state of several cysteine residues. Cys226, 613, 622, and 624, are sensitive to $H_2O_2$, upon oxidation these cysteine groups form disulfide bonds (FIG. 2) which trigger the release of Nrf2 into the nucleus to activate ARE-dependent transcription (40, 41).

The previously mentioned Cys residues form disulfide bonds through an oxidative mechanism. However, an additional route may also be possible.

If a thiol is presented with a polysulfide ($HS_xH$), anionic compounds that are composed of short sulfur chains typically two to three but fewer than 8 atoms long. The thiolate can attack the most electrophilic sulfur in the chain because thiolates are nucleophilic (42). This reaction produces a conjugate species with the polysulfide and displaces HS—, and forms a persulfide (R—SSH). The persulfide is susceptible to nucleophilic attack by adjacent cysteine residues that forms a disulfide bond and displaces a second HS— (42) (FIG. 2).

Here, we demonstrate that OCNPs oxidize $H_2S$ to polysulfides and that they are capable of increasing free Nrf2 in cultured bEnd.3 cells, alone and potentiated when cotreated with lipoic acid, a cell-mediated $H_2S$ donor (43). Cotreatment of bEnd.3 cells with OCNPs results in a distinct increase in free Nrf2 after 1.5-3 hours of incubation. This effect is consistent with our proposed mechanism of action that OCNPs catalyze the formation of polysulfides ($HS_xH$), enhanced in the presence of lipoic acid, which facilitate the stabilization of Nrf2 and thus lead to elevated Nrf2 levels.

An additional potential mechanism in DS, the third copy of chromosome 21 introduces a third copy of the transcription regulator BTB Domain and CNC Homolog 1 (BACH1) that competes with Nrf2 for ARE binding domains (FIG. 2) (44). BACH1 does not promote ARE-dependent enzyme expression and thus the antioxidant response to an oxidative stress event is downregulated (FIG. 2). Normally, BACH1 acts as a negative regulator for AREs, when heme binds to BACH1 in the nucleus, BACH1 dissociates from AREs and allows Nrf2 to bind in its place (44). However, with a higher concentration of BACH1, this effect is less pronounced and fewer Nrf2-ARE binding events occur relative to BACH1-ARE binding events (FIG. 3).

Dysregulation of the BACH1-Nrf2 axis has been suggested for involvement in the development of Alzheimer's disease in individuals with DS (45). It is our view that the increased cytosolic level of free Nrf2 competes more effectively against the excess of BACH1, preventing some of the pathway dysfunction. Thus, there are multiple potential beneficial effects of OCNPs, including when potentiated by lipoic acid, on the Nrf2 mechanism of treating these deficits in DS.

The inventors and co-workers developed a synthetic method to produce biologically potent oxidized carbon nanoparticles (OCNPs) from various carbon sources (U.S. Pat. No. 9,572,834) (20, 46-48). Originally, it was thought these nanoparticles were only superoxide dismutase mimetics, but it has now been discovered that the particles' stable electron radical and structure catalyzed other reactions as well, including transferring electrons between mitochondrial constituents (48) and now most recently, production of polysulfides (FIGS. 4A-4E).

Therefore, the OCNPs qualified as newly conceptualized "nanozymes" or nanoparticles that act as redox mediators in biological reactions (48). These particles, most recently derived from medicinal grade activated charcoal (7), are 3-8 nm in diameter and PEG(ylated) for enhanced in vivo distribution and uptake by cultured cells and mitochondrial localization.

The inventors and co-workers recently found that OCNPs also accelerate the formation of polysulfides derived from $H_2S$ (in the form of $Na_2S$) in solution (FIG. 4A) and endogenously in HEK293 cells (FIG. 4B).

Fluorescence microscopy showed that bEnd.3 cells treated with OCNPs and labeled with SSP4 have a higher average integrated fluorescence (sum of all fluorescence within the cell) than those without treatment or with AP39 (FIG. 4C). Preliminary data also show this action has functional consequences as OCNPs reduced both the proliferative and toxic effects of AP39 across a range of 10-1000 nM (FIG. 4D).

OCNPs also increase the rate that thiosulfate is produced indicating that the resulting oxidized products should be excreted readily through the kidneys (FIG. 4E). This new action has major importance because, while $H_2S$ has little biological actions on its own, its polysulfide products are excellent antioxidants and have critical biological roles in persulfidation reactions (23). These results suggest that OCNPs can protect DS-donor cells from an endogenous overexpression of CBS with polysulfides and thiosulfate as products.

The composition of OCNPs affords the use of facile amide coupling between the carboxylic acid functional groups on the OCNP and the amine functional group on a conjugating molecular species. We demonstrated the feasibility of this approach previously (50, 51, U.S. Patent publication 2020/0222453) where we conjugated deferoxamine to hydrophilic carbon clusters (HCC) to imbue the HCCs with the capacity to chelate iron (III). Because conjugating an amine-terminated molecule to the OCNP has been shown to be feasible, it stands that other molecules can also in kind be conjugated the same way directly or through a linker molecule. In addition, esterification through the carboxylic acid functional groups to alcohols, or acyl chlorides on a conjugating molecule to the particle hydroxyls, either directly, or through a linker is also contemplated. This aspect is also discussed further hereinafter.

Coupling lipoic acid to the OCNP may imbue the particle with the capacity to produce hydrogen sulfide near the particle and therefore generate polysulfides more efficiently, these reactive sulfur species products can then be used to persulfidate other disulfides such as those on the regulatory protein Keap1.

It is our view that the increased cytosolic level of free Nrf2 competes more effectively against the excess of BACH1, preventing some of the pathway dysfunction. Thus, there are multiple potential beneficial effects of OCNPs particularly when potentiated by lipoic acid, on the Nrf2 mechanism of treating these deficits in DS.

BRIEF SUMMARY OF THE INVENTION

The present invention contemplates a new approach to treating a Down syndrome subject presenting with a functional decline or at risk of organ systems associated with accelerated aging due to over-production of $H_2S$. The treatment contemplates administering a pharmaceutical composition containing a hydrophilic polymer-substituted oxidized carbon nanoparticles (OCNPs) such as poly(ethylene glycol)-functionalized oxidized activated charcoal (PEG-OAC) and an optional potentiating amount of lipoic acid or dihydrolipoic acid to the Downs subject. The particles catalytically dismutate superoxide, oxidize $H_2S$ to form polysulfides and shuttle electrons between mitochondrial constituents (20). These specially synthesized hydrophilic polymer-substituted OCNPs are protective in a variety of acute brain injury animal models with no appreciable toxicity (21, 22).

A pharmaceutical composition is contemplated that contains an $H_2S$-reducing effective amount of hydrophilic polymer-substituted oxidized carbon nanoparticles (OCNPs) such as poly(ethylene glycol)-functionalized oxidized activated charcoal (PEG-OCNPs or PEG-OAC) dissolved or dispersed in a physiologically acceptable diluent.

A treatment can involve co-administration of an optional amount of molecules including those that potentiate the beneficial effects of the OCNPs, such as lipoic acid or its derivatives. These co-administered molecules can be administered separately or directly bound to the OCNP through chemical means.

A treatment method is typically repeated.

The invention further includes stratification of DS individuals by one or more of levels of $H_2S$ and/or its metabolites in blood and/or urine, evidence of oxidative injury through measurement of well-established markers including lipid peroxidation, DNA oxidative damage and other methods. Because decline in DS involves multiple organ systems, treatment effect is monitored by clinical endpoints and laboratory and biochemical endpoints including cellular respiration, homocysteine, cysteine, methyl-tetrahydrofolate, amyloid precursor protein, lipid peroxidation, and glutathione tissue and circulating concentrations.

The clinical endpoints include but not restricted to muscle strength, cardiac function, cognitive function through established testing procedures procedure. Laboratory endpoints include but not restricted to bone density, brain imaging. Biochemical tests include levels of $H_2S$ and its metabolites in blood and/or urine, proliferation of individual cells studied ex-vivo, mitochondrial energetics, resistance ex-vivo of cells to exogenous toxins such as hydrogen peroxide, excess $H_2S$ such as by high concentrations of $H_2S$ donors such as AP39. Long term clinical markers will include but not restricted to history of bone fractures, change in cognitive function through administered testing, evidence of brain atrophy or signs of Alzheimer Disease, overall level of functioning and wellbeing through testing procedures.

BRIEF DESCRIPTION OF THE DRAWINGS

In the drawings forming a portion of this disclosure,

FIGS. 4A through 4E illustrate the effect of OCNPs on polysulfide formation from $Na_2S$ and AP39. FIG. 4A illustrates that hydrophilic polymer-substituted oxidized carbon nanoparticles (OCNPs) increase the rate of polysulfide formation (y axis) from $Na_2S$ in solution 30× compared to the background rate (WO 2021/252,382 FIG. 10A). FIG. 4B illustrates that polysulfide production in HEK293 cells (y axis) is catalyzed by OCNPs in a dose-dependent manner. FIG. 4C is a bar graph that shows the average integrated fluorescence of bEnd.3 cells treated with 8 μg/mL OCNPs or 5 υM AP39, and that particles alone enhance polysulfide production. FIG. 4D shows that OCNPs normalize bEnd.3 cell proliferation from the opposing effects of 10 and 1000 nM of the mitochondria-targeting $H_2S$ donor, AP39. FIG. 4E shows that thiosulfate ($S_2O_3^{2-}$) production (y axis) increase is dose-dependent relative to PEG-OAC concentration (x axis) (WO 2021/252,382 FIG. 14).

FIG. 6 shows a schematic synthesis of PEG-OAC. Here, U.S. Food and Drug Administration Good Manufacturing Practice (GMP) AC is oxidized via fuming nitric acid at a temperature of 100° C. for 6 hours (h) or for 4 h if the particles were sieved prior to the initial oxidation, and followed by PEGylation, where “DIC” is N,N'-diisopropylcarbodiimide and “n” is a number whose average value is about 60 to about 250.

DETAILED DESCRIPTION OF PREFERRED EMBODIMENTS

The present invention contemplates a method for treating a Down syndrome (DS) subject presenting with or at risk of functional decline of organ systems associated with accelerated aging due to over-production of $H_2S$. The method comprises administering a pharmaceutical composition containing a $H_2S$-reducing effective amount of hydrophilic polymer-substituted oxidized carbon nanoparticles (OCNPs) and an optional potentiating amount of lipoic acid or dihydrolipoic acid dissolved or dispersed in a physiologically acceptable diluent to the subject. The administration is normally reported.

Because $H_2S$ levels can reflect heterogeneity in the expression of CBS, stratification of DS individuals by $H_2S$ levels can be used to identify those at highest risk for deterioration due to $H_2S$. We contemplate the clinical application of our therapeutic approach to a personalized approach based on $H_2S$ levels and measures of oxidative stress, to be measured in blood using established methods including but not limited to: gas chromatography (27), methylene blue detection of $H_2S$, dibimane detection of $H_2S$ (29), as can those several further markers of over production of $H_2S$ and oxidative stress noted elsewhere herein.

Thus, such markers can be used as a basis for providing preventative treatment of a DS subject prior to the time that functional decline of organ systems is identified. Such preventative treatments utilize a pharmaceutical composition that is the same as that described above.

The inventors and co-workers developed a synthetic method to produce biologically potent oxidized carbon nanoparticles (OCNPs) from various carbon sources (U.S. Pat. No. 9,572,834; WO 2021/252,382) (20, 46-48). Originally, it was thought these nanoparticles were only superoxide dismutase mimetics, but it has now been discovered that the particles' stable electron radical and structure catalyzed other reactions as well, including transferring electrons between mitochondrial constituents (48) and now most recently, production of polysulfides (FIGS. 2A-2E).

Therefore, the OCNPs qualified as newly conceptualized "nanozymes" or nanoparticles that act as redox mediators in biological reactions (29). These particles, most recently derived from medicinal grade coconut activated charcoal (20), are typically about 2 to about 5 nm in diameter and PEG(ylated) for enhanced in vivo distribution, uptake by cultured cells and mitochondrial localization and in vivo half-life prior to elimination.

Figure 4B:
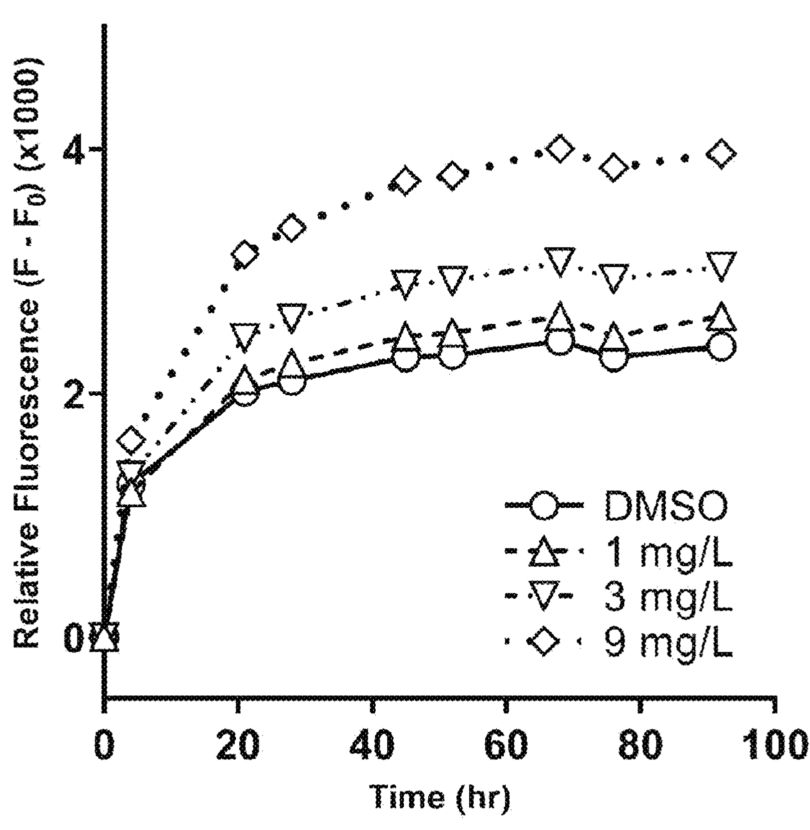
Figure 4C:
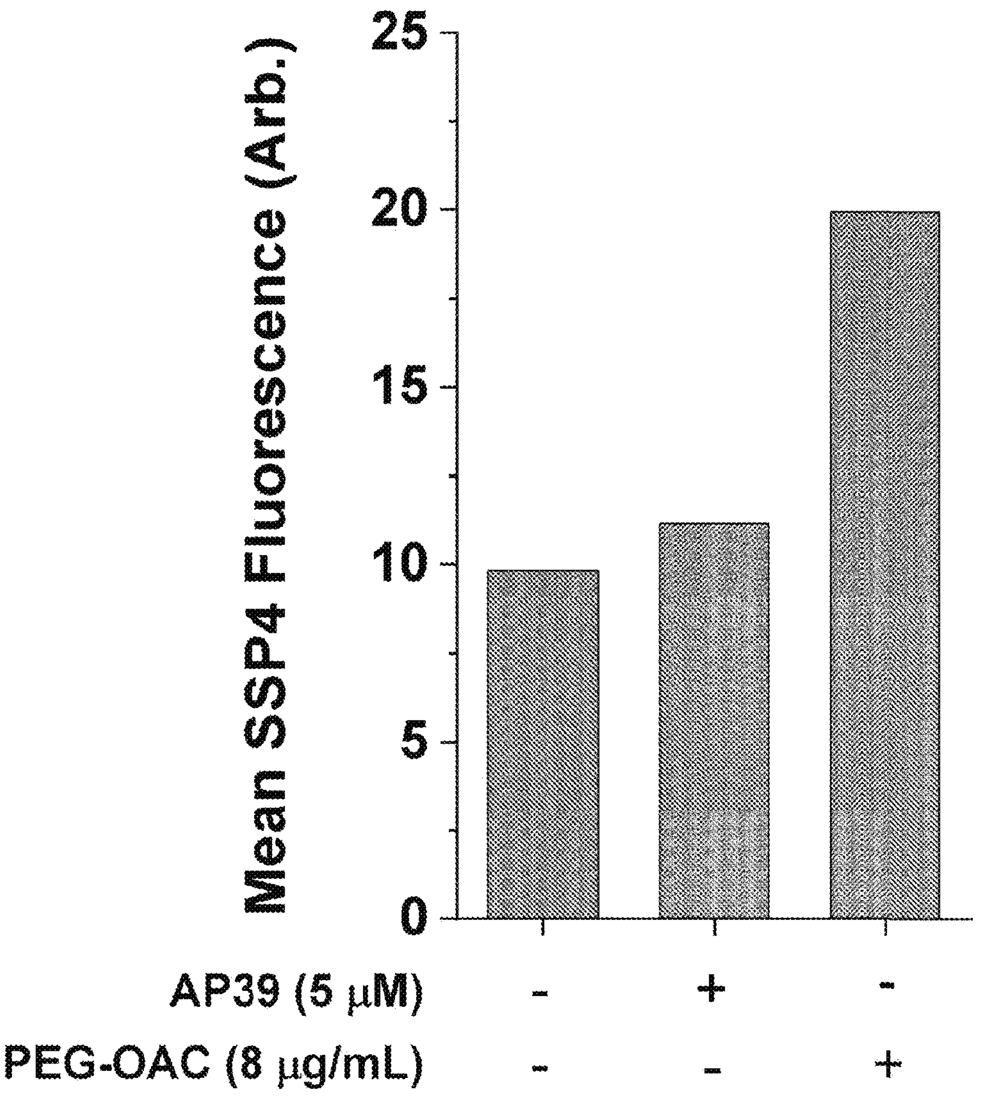
Figure 4D:
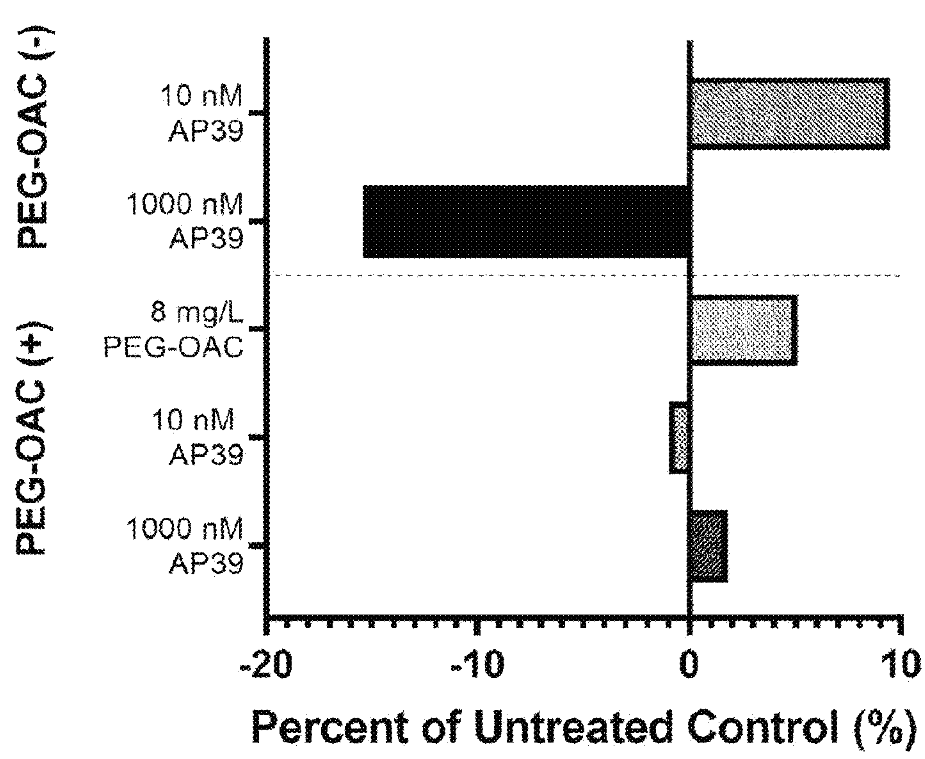

The inventors recently found that PEG-OCNPs (PEG-OAC) also accelerate the formation of polysulfides derived from $H_2S$ (in the form of $Na_2S$) in solution (FIG. 4A) and endogenously in HEK293 (human embryonic kidney cells; ATCC CRL-1573™; FIG. 4B). The mean fluorescence from bEnd.3 cells treated with OCNPs (FIG. 4C) showed that OCNPs potentiated the formation of endogenous polysulfides derived from $H_2S$ generated by the mitochondrial $H_2S$ donor AP39, and without any additional $H_2S$ (FIG. 4C). Preliminary data show this action has functional consequences as OCNPs reduced both the proliferative and toxic effects of AP39 across a range of 10-1000 nM (FIG. 4D).

Converting $H_2S$ to polysulfide has beneficial effects because polysulfides quench reactive oxygen species (ROS) (23), promote critical persulfidation reactions (19), and reduce disulfides back to thiols (24). After quenching the ROS, polysulfides are converted to benign thiosulfate ($S_2O_3^{2-}$) that is excreted (25).

Figure 4E:
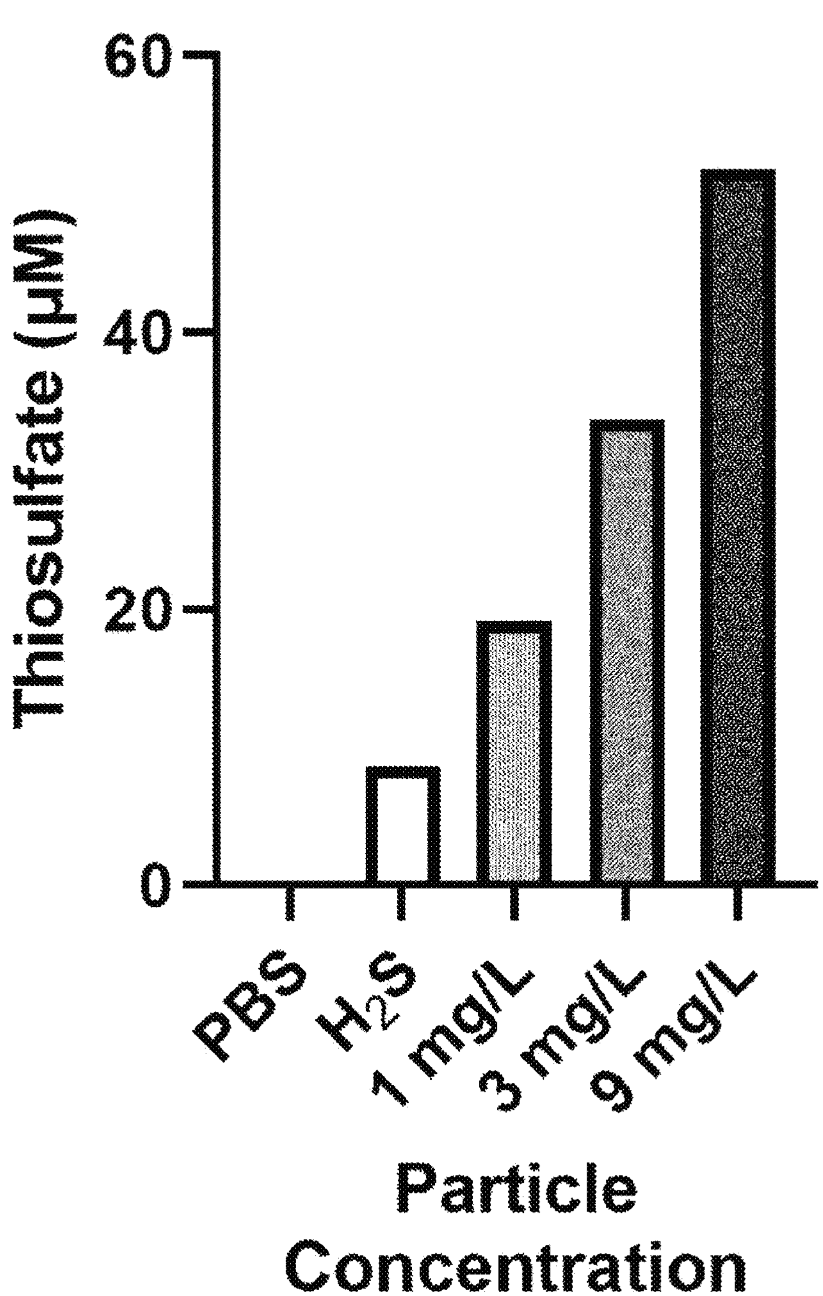

OCNPs also increase the rate that thiosulfate is produced indicating that the resulting oxidized products should be excreted readily through the kidneys (FIG. 4E). This new action has major importance because, while $H_2S$ has little biological actions on its own, its polysulfide products are excellent antioxidants and have critical biological roles in persulfidation reactions (23). These results suggest that OCNPs can protect DS-donor cells from an endogenous overexpression of CBS with polysulfides and thiosulfate as products.

Channeling excess $H_2S$ into polysulfides is an attractive therapeutic method to protect mitochondria and preserve neurological and other organ system function in DS and other conditions. Most proposed approaches involve scavenging or inhibiting $H_2S$ production, which is fraught with difficulty because although $H_2S$ has little actions on its own, some level is needed to generate these active metabolites. It is contemplated that OCNPs will reduce ROS load and restore the metabolic imbalance caused by an excess of CBS and $H_2S$.

Figure 1:
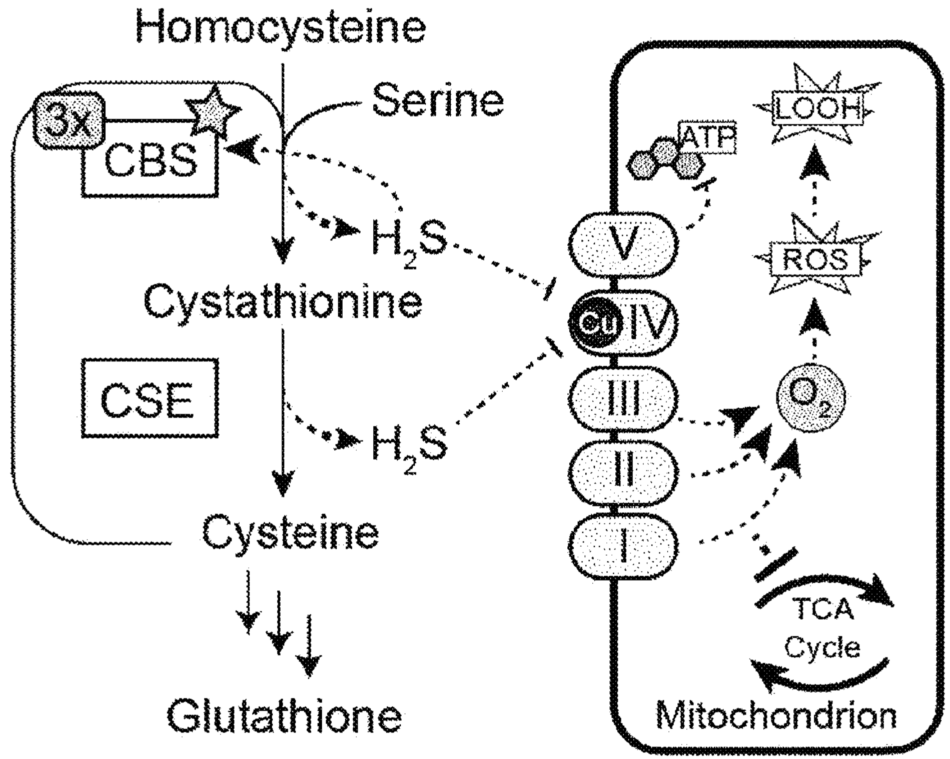
FIG. 1 is a schematic depiction of the effects of cystathionine-β-synthase (CBS) overexpression on mitochondria. Overexpression of CBS causes an excess of $H_2S$, which in turn causes a cascade of toxic effects mediated in part by impairment of mitochondria by Complex IV inhibition. This reduces ATP production, elevates reactive oxygen species (ROS) and lipid peroxides (LOOH) and impairs the tricarboxylic acid cycle (TCA).

Endogenous $H_2S$ is produced primarily through the transsulfuration pathway by cystathionine-β-synthase (CBS) and cystathionine-γ-lyase (CSE) (31) (FIG. 1). The roles of $H_2S$ in the body are varied, however a dysregulated excess is universally detrimental (32). In mitochondria, excess $H_2S$ impairs Complex IV which causes electron leakage due to the inability for oxygen to capture electrons from upstream Complexes (33). Inhibition of the electron transport chain (ETC) leads to an increased dependence on glycolysis (16) and reduction in ATP production.

DS was identified as a new disease target due to the presence of elevated $H_2S$ caused at least in part by the overexpression of CBS due to the presence of a third chromosome 21 (trisomy). These effects of Complex IV impairment have been observed in humans, including a glycolytic shift and reduction in ATP (52). The trisomy is present in all of a subject's cells except, possibly, the gametes. Thus, substantially any cells can be used as illustrative of the effect of trisomy. We have selected to use lymphocytes and fibroblasts as illustrative as they are relatively plentiful and easily obtained with little pain or nuisance to the donating human subject.

It is believed that OCNPs administration, by enhancing the generation of antioxidant polysulfides and thiosulfates, can improve oxidative phosphorylation, reduce dependence on glycolysis, and reduce oxidative stress in cells carrying the DS mutation.

The conversion of $H_2S$ to antioxidant polysulfides has not been presented as a potential therapeutic method for reducing excessive $H_2S$ such as in DS. Direct inhibition of CBS has been proposed as a potential means of reducing $H_2S$ biogenesis and a number of CBS inhibitors have been developed yet none have been shown to be pharmacologically useful (53). Because CBS produces essential amounts of cysteine that can be used to produce glutathione, direct inhibition of the enzyme may not be desirable.

We illustrate that OCNPs reduces oxidative stress and enhances the health of DS-patient derived lymphocytes. We employ models of endogenous $H_2S$ excess in DS-derived cell lines and drug-induced $H_2S$ excess in apparently healthy (AHI), age-matched cells.

Polysulfide and $H_2S$ levels are followed by the indicators Sulfur Sensing probe 4 (SSP4) and 7-azido-4-methylcoumarin (AzMC), respectively. ROS levels are determined employing MitoSOX™ mitochondrial superoxide indicator (Fisher Scientific) and CellROX® (Life Technologies, Inc.) indicators. Oxygen consumption by DS- and AHI cell lines and effects of OCNPs is performed utilizing the Agilent Seahorse mitochondrial function test.

Because it is possible that DS cells in vitro are inherently stressed and to demonstrate the beneficial effects of OCNPs, we determined whether OCNPs can directly protect DS-derived cells from superimposed mitochondrial oxidative stress caused by hydrogen peroxide. Here, we compare DS-derived cells to apparently healthy individuals (AHI) cells (FIG. 15A), and studied the differences in oxygen consumption as a marker of mitochondrial function, superoxide production, oxidative stress, and cell survival as measures of cell health.

Figure 5:
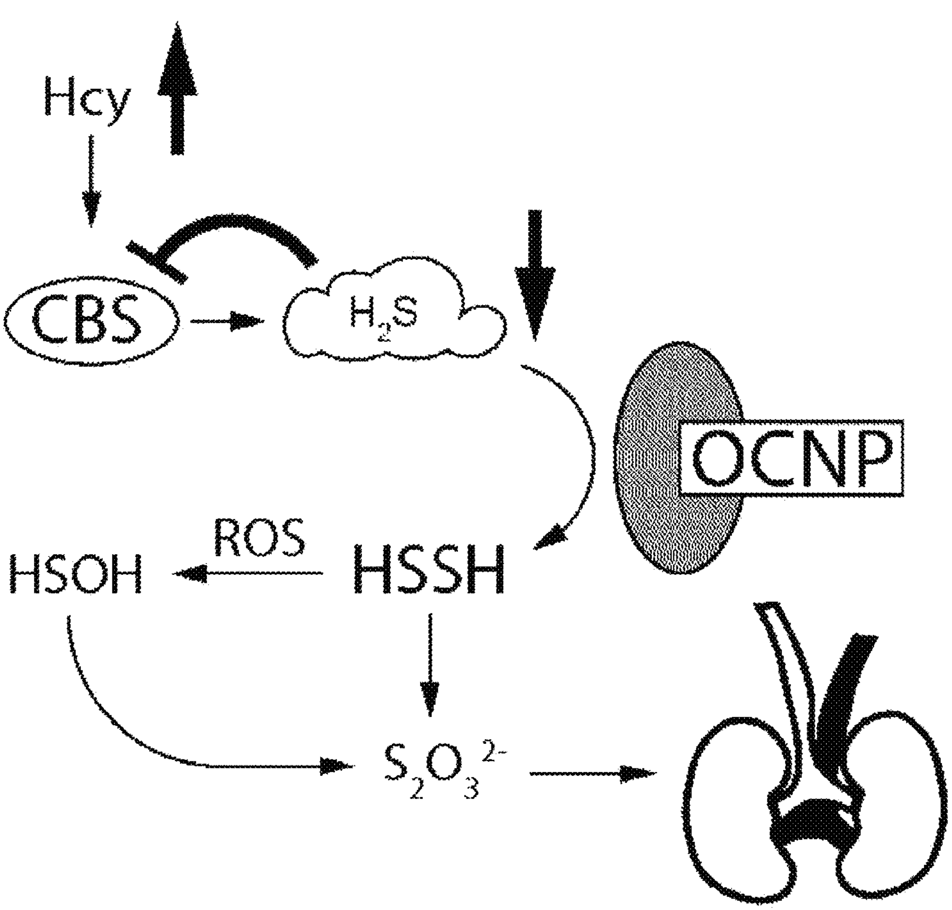
FIG. 5 is a schematic drawing that illustrates a mechanism of action by OCNPs on CBS regulation. OCNPs converts $H_2S$ to polysulfides (HSSH), which may reduce activation of CBS. HSSH reduce ROS, and thiosulfate products are removed via the kidneys. In sum, the effect of $H_2S$ over-production is mitigated by increasing the rate of its oxidation.
Figure 7:
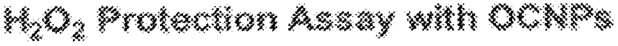
FIG. 7 is a bar graph depicting the protective capacity of PEG-OACs against hydrogen peroxide in bEnd.3 cells. Y-axis: control normalized cell count (100%). PEG-OACs (8 mg/L) protect bEnd.3 cells from death at 24 hours caused by 100 μM $H_2O_2$ ($P<0.001$).
Figure 7:
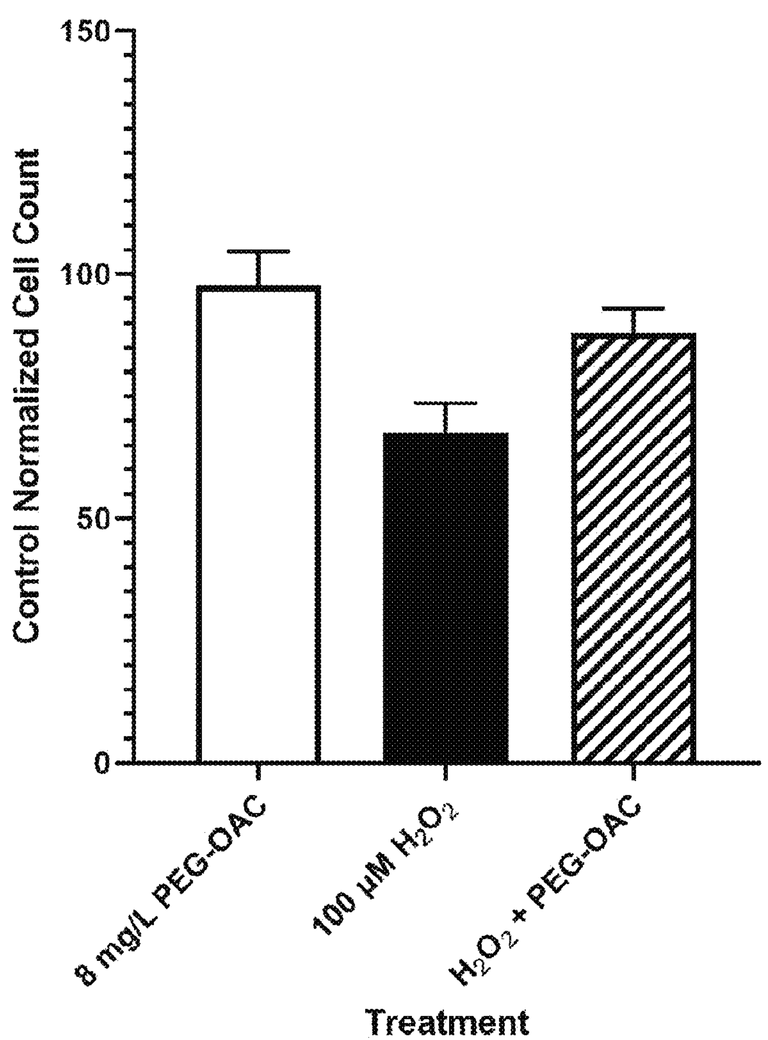

Here, we find that OCNPs can oxidize $H_2S$ to polysulfides that reduce the positive feedback activation loop between CBS and $H_2S$ (FIG. 5). Introducing a catalyst to treat this disease is a conceptual shift from more traditional ligand-target inhibition to the use of chemically active nanocatalysts that act to enhance desired products.

Figure 6:
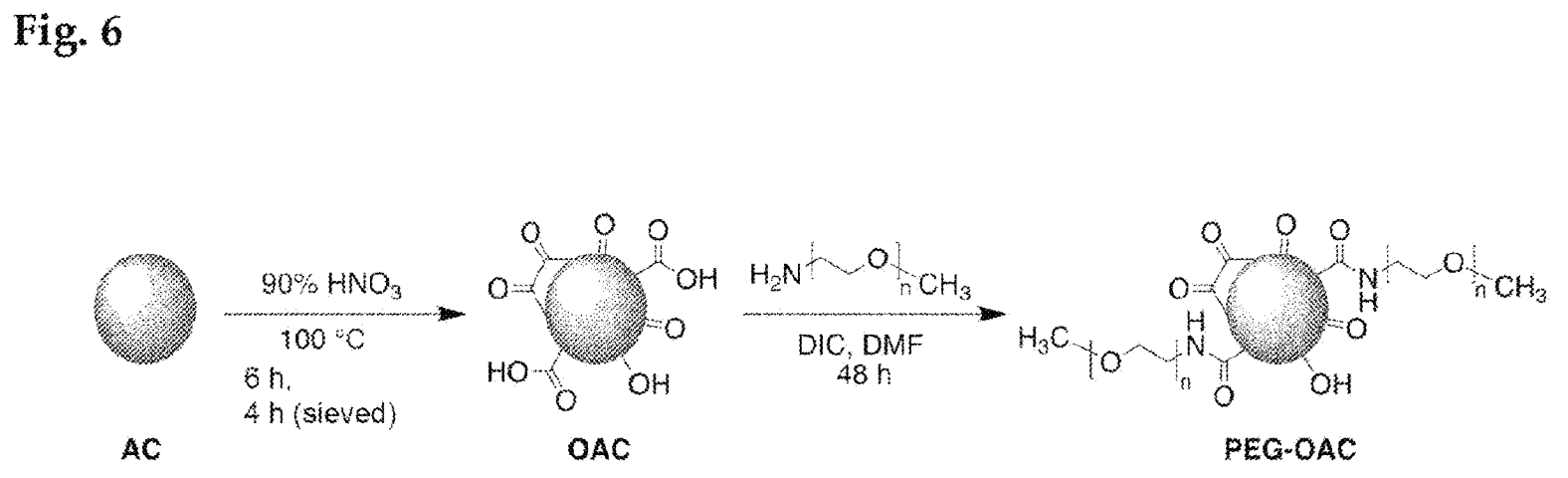

The illustrative OCNPs used in the present studies are PEGylated as illustrated in FIG. 6 and discussed hereinafter. The omega-methoxy poly(ethylene glycol) amine used can have a molecular weight of about 2000 to about 10,000 Da. Mixtures of these PEG derivatives having differing molecular weights can also be used. It is presently preferred to use an omega-methoxy poly(ethylene glycol) amine having an average molecular weight of about 5000 Da in the syntheses of a PEG-OAC preparation.

It is to be understood and is well known in the art that the commercially available PEG products are mixtures of differing molecular weights due to the differing number of ethylene glycol repeating units present. Thus, in a PEG product having a molecular weight of about 2000 Da, there are an average of about 60 repeating units ("n" in FIG. 6). In a PEG product having a molecular weight of about 5000 Da, there are an average of about 125 repeating units, whereas in a PEG product having a molecular weight of about 10,000 Da, there are an average of about 250 repeating units.

The number of PEG substituents on each particle also varies among the particles of a given preparation. An average of about 3 to about 12 PEG substituents are present per particle, and preferably an average of about 5 to about 10. These numbers can be determined by thermogravimetric analysis.

PEG-OACs are synthesized using the procedure as previously described (20) and illustrated hereinafter. In brief, particles are preferably synthesized from coconut-derived activated charcoal (cAC) and oxidized with fuming nitric acid (90% $HNO_3$) followed by conjugation with amino-poly (ethylene glycol) that produces carbon core particles, mean about 3 nm diameter. The coconut AC is obtained from the manufacturer as a powder of varying average longest dimension. In one embodiment, the as-provided powder is passed through a sieve having a 20 μm opening (U.S. Standard No. 635 openings) prior to the oxidation step to provide oxidation product of greater uniformity of particle size.

The particles are discoid in shape and form a non-separating dispersion in water at a concentration of about 1 to about 5 mg/mL. The dispersion is stable to separation at ambient room temperature for at least seven days. The oxidized carbon nanoparticulate dispersion in water exhibits an UV absorbance maximum at about 220 nm. The particles contain about 9 to about 15 percent carbonyl groups by X-ray photoelectron spectroscopy (XPS), and pass through a 0.22 μm pore size polyethersulfone (PES) filter membrane (WO 2021/252382).

In addition to PEG-substituted OCNPs, additional substituents can also be present bonded to the carboxylic acid, hydroxyl and ketone functionalities present as part of the OCNPs due to their oxidative synthesis. Thus, propylene oxide polymers [poly(propylene glycol); PPG] can also be used, as can propylene oxide-ethylene oxide copolymers where it is desired to utilize a somewhat less hydrophilic, but still water-solubilizing/dispersing substituent.

Figure 13:
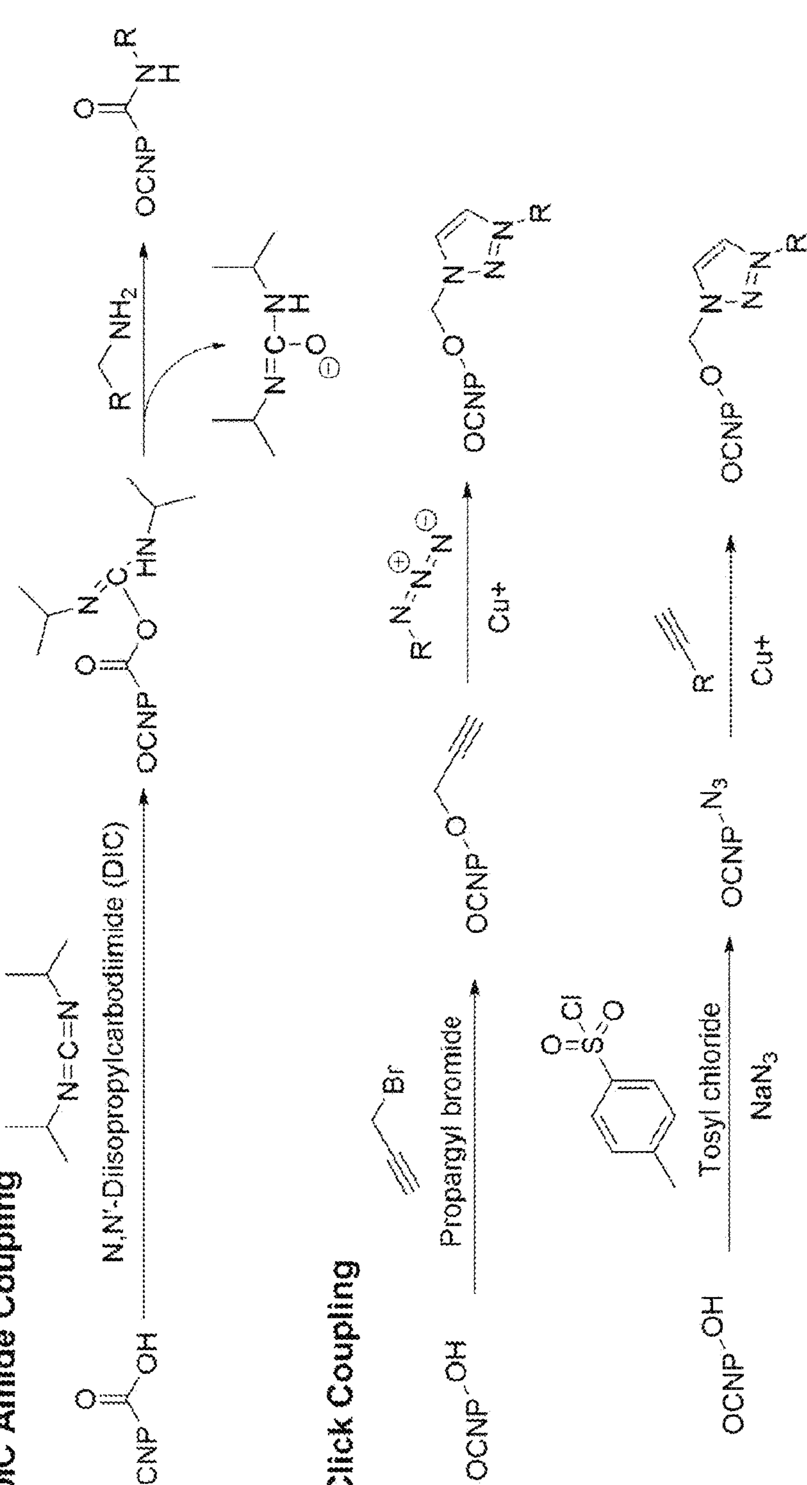
FIG. 13 shows two reaction schemes of coupling methods to attach ligands to OCNPs on either the carboxylic acid or phenol functional groups using amide-coupling, or ‘click’ chemistry coupling for appending additional ligands to OCNPs.

Two types of substituent-bonding reactions are illustrated schematically in FIG. 13. The upper scheme illustrates the use of a particle carboxylic acid functionality to form an amide bond with a primary amine-containing substituent group, R, such as omega-methoxy poly(ethylene glycol) amine. The lower two schemes utilize a hydroxyl group present on the particle to initiate reactions used in "clck coupling", where the substituent, R, is contains a terminal alkyne group.

Hydrophilic substituents that provide an ionic charge at physiologic pH values are not usually utilized because ionically-charged species frequently do not penetrate cell walls, whereas OCNPs bonded to uncharged substituents such as PEG can and do penetrate cells and also pass through the blood-brain barrier. (See, FIG. 14.)

Particles are characterized by dynamic light scattering (DLS), thermogravimetric analysis (TGA), transmission electron microscopy (TEM), cyclic voltammetry (CV), and Fourier Transform Infrared Spectrometry (FT-IR) to ensure the consistency of the product. The OCNP particles are stable in PBS, cell culture media, an important consideration for translational research.

Figure 14:
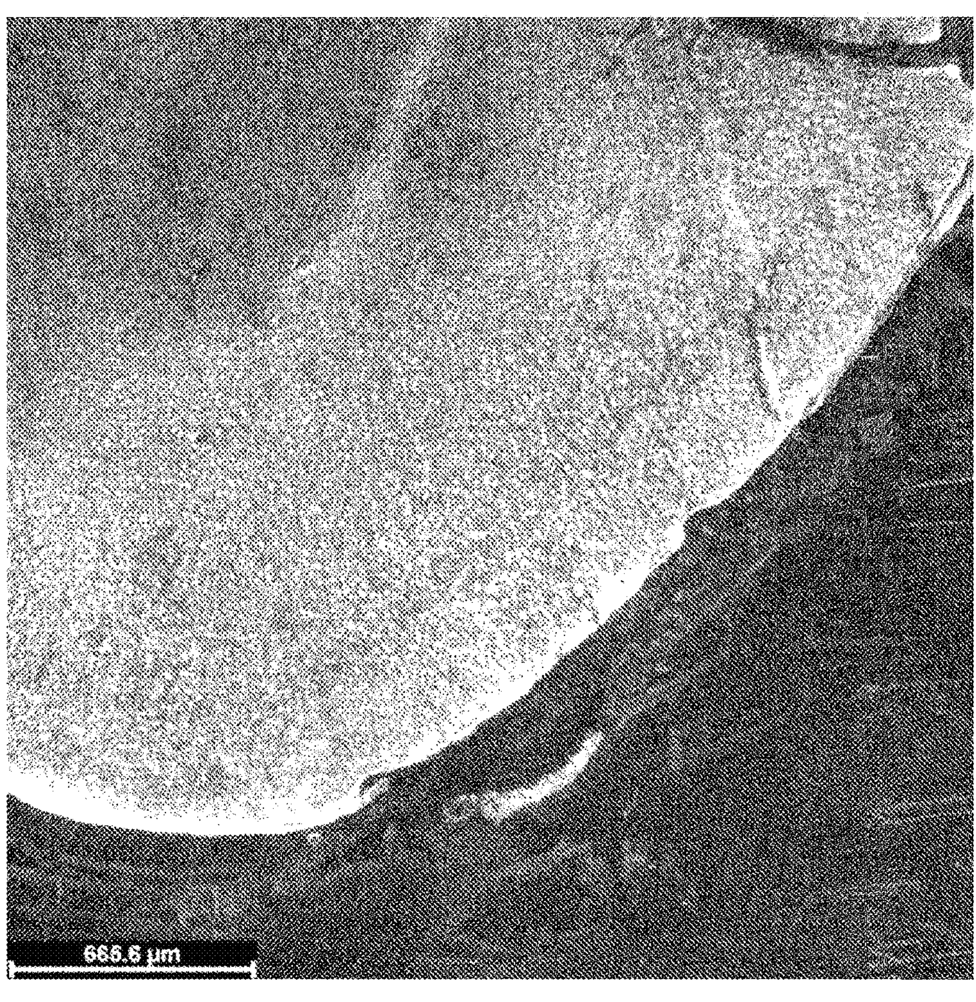
FIG. 14 is a photomicrograph of a section of rat brain obtained from a Sprague Dawley rat euthanized 24 hours after parental treatment of 2 mg/kg PEG-OACs. After fixation in 4% formaldehyde, the tissue was labeled with anti-poly(ethylene glycol) antibody and AlexaFluor 647-labeled IgG antibody. The brightness indicates the amount of poly (ethylene glycol) at that location as indicated by the AlexaFluor 647-labeled IgG secondary antibody.

Using poly(ethylene glycol)-specific antibody labeling we have preliminarily found that PEG-OACs are able to reside in rat brain (FIG. 14).

We found that PEG-OACs abolished both the proliferative and toxic effects of mitochondrial $H_2S$ donor AP39 (FIG. 4D). Here, PEG-OACs protect bEnd.3 cells from excess $H_2S$ and show both improved survival and normalized proliferation in bEnd.3 cells.

Age-matched and sex-matched DS-donor and apparently healthy individual (AHI) lymphocytes (Coriell Institute, Camden, NJ) are used as a human model of DS. We examined the effect of AP39, a mitochondria-targeted drug to induce excess $H_2S$ in normal cells and compare them to DS cells with and without OCNPs. To measure changes in proliferation, DS- and AHI-donor cells are treated for 1-5 days with and without PEG-OACs (4 mg/L), afterwards they are counted by hemocytometer.

Figure 10:
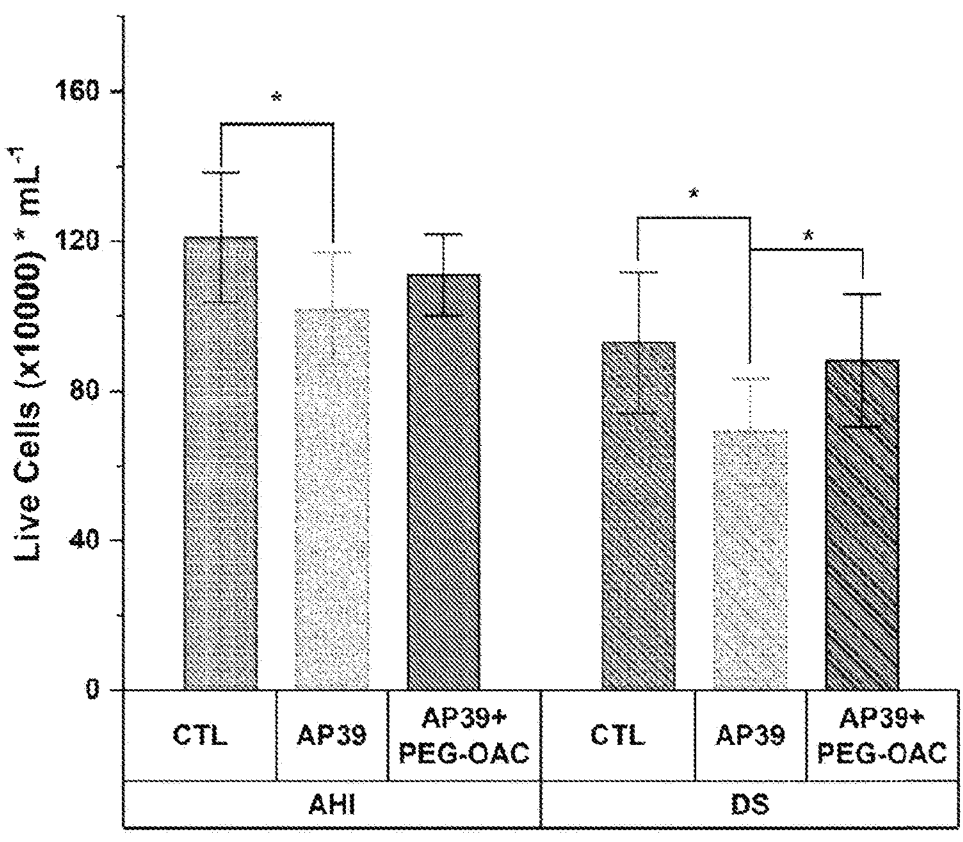
FIG. 10 shows the effect of PEG-OACs on AHI and DS lymphocytes when treated with AP39, a mitochondria-targeting H2S donor. AHI and DS cell proliferation is reduced with 5 μM AP39 ($p<0.05$). Proliferation was partially restored by PEG-OAC in the AHI cells [GM01954 (F, 44); GM14592 (M, 41); and GM25522 (F, 37)]. For the DS cells [AG10317 (F, 37); AG09802 (M, 41); AG09394 (M, 2); and GM01921 (M, 23)], a significant reduction in viability was noted between the untreated control and the AP39-treated cells ($p<0.05$) which was significantly improved in the presence of PEG-OACs ($p<0.05$).

We observed that OCNPs protected the cells compared to the AP39 treatment alone (FIG. 10). To measure changes in $H_2S$ production, cells are treated with PEG-OACs simultaneously with 7-azido-3-methylcoumarin (AzMC) and the appearance of AzMC fluorescence is measured over 24 hours based on previous work.

Figure 2:
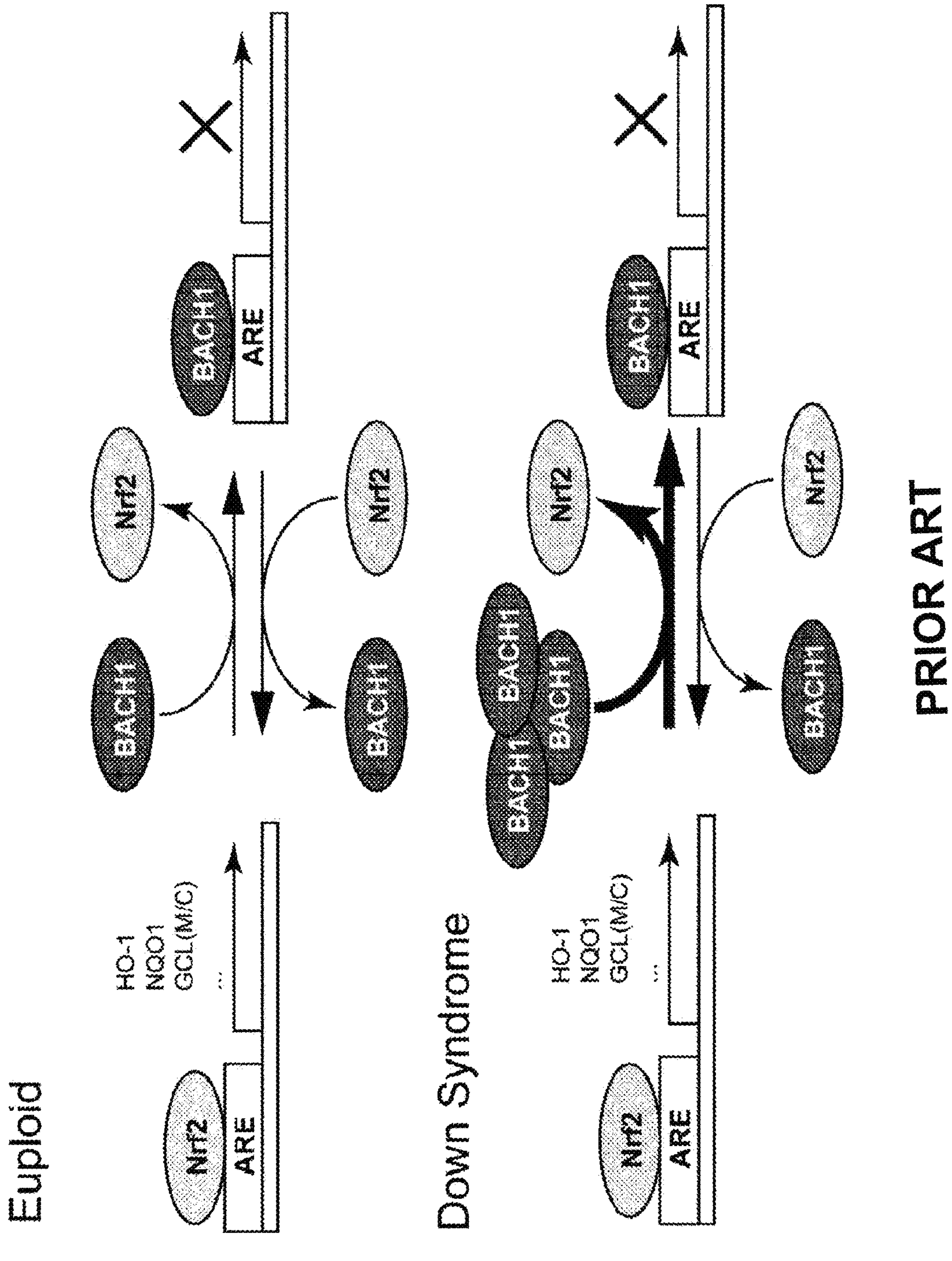
FIG. 2 is a schematic depiction of Nrf2 activity depletion by the overexpression of BACH1 found in Trisomy 21 (Down syndrome; DS) as compared to the similar activity in cells of normal chromosome number (Euploid). Nrf2 and BACH1 are in equilibrium for the antioxidant response elements (AREs) which promotes the transcription of several antioxidant enzymes. In DS, excess BACH1 (thick arrows) displaces Nrf2 and prevents the transcription of ARE-related enzymes.
Figure 3:
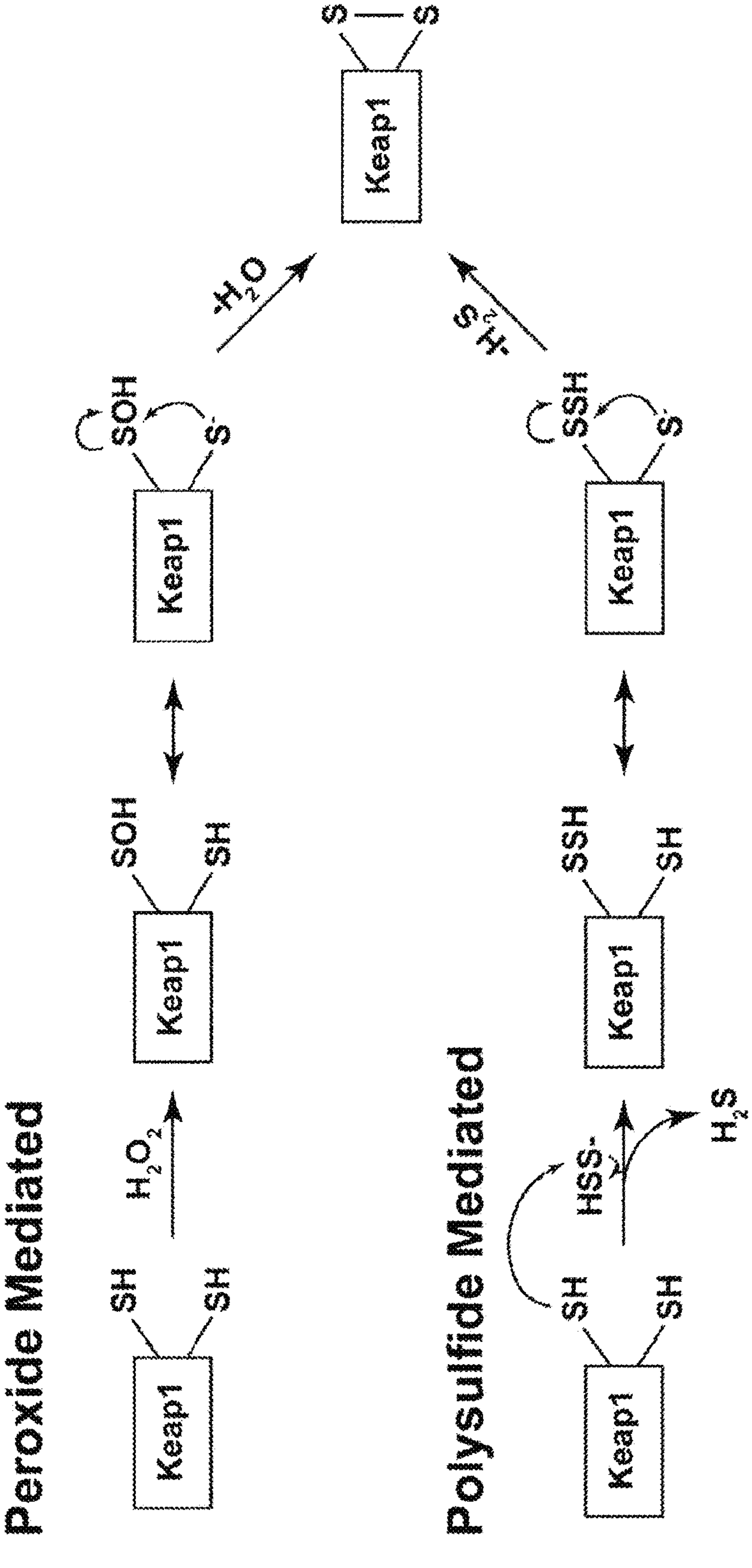
FIG. 3 is a reaction schematic of how the cysteine amino acids of Keap1 that respond to hydrogen peroxide can also react with polysulfides. The mechanism is analogous but is mediated via a sulfur-driven route.

Likewise, polysulfide synthesis is measured by cotreatment of the cells with PEG-OACs and SSP4 and the appearance of a fluorescent signal (FIGS. 2B, 2C and 4A). $S_2O_3^{2-}$ production is measured by taking daily aliquots of the culture media over the course of 5 days and adding $S_2O_3^{2-}$ specific tannic acid-functionalized silver nanoparticles by Dong et al. (30).

Figure 12C:
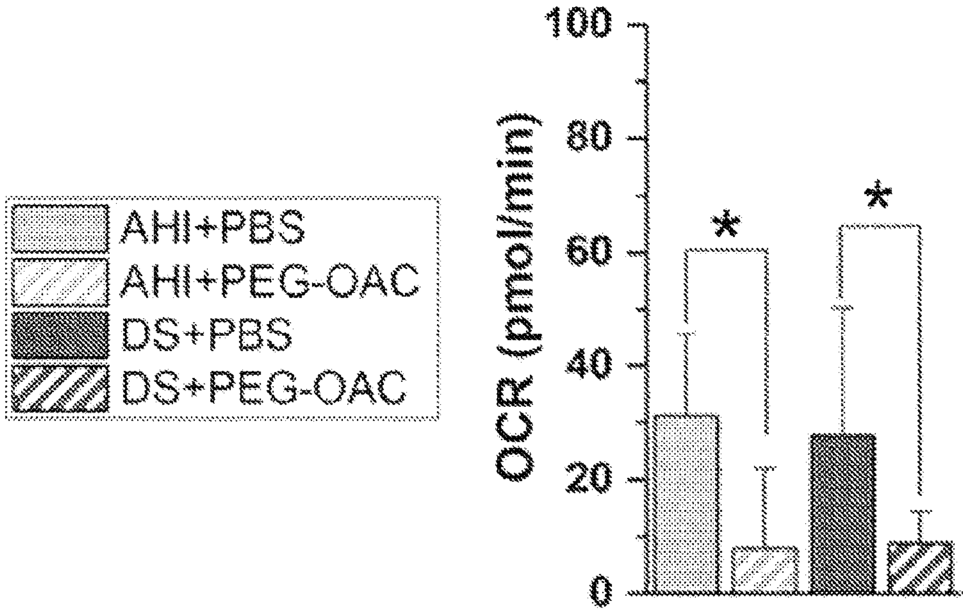
FIG. 12, in eight panels as FIGS. 12A through 12H, show the calculated output of an Agilent Seahorse XFe96 study using AHI and DS lymphocytes.
FIG. 12A, a chronological plot of oxygen consumption rate (OCR) by DS and AHI lymphocytes shows when the inhibitors oligomycin, FCCP, rotenone and antimycin A are added. From these inhibition treatments, several metabolic parameters can be obtained.
FIG. 12B shows basal oxygen consumption rate (OCR) in DS donor lymphocytes was higher than those of the AHI donor lymphocytes and both the AHI and DS donor lymphocytes increased OCR when contacted by PEG-OACs (FIG. 12B) to a somewhat greater extent in the DS cells. The calculated proton leak (FIG. 12C), the amount of OCR associated with protons returning to the matrix without driving Complex V, of AHI and DS donor lymphocytes were reduced by the PEG-OACs, showing a marked decrease in proton leak. Likewise, ATP production was also increased in the PEG-OAC treated cells (FIG. 12D). Maximal respiration (FIG. 12E) and spare respiratory capacity (FIG. 12F) were not affected in the AHI cells but dramatically increased in the PEG-OAC treated DS cells. Nonmitochondrial respiration was not significantly affected regardless of treatment (FIG. 12G). Finally, coupling efficiency was improved in both the AHI and DS cell lines (FIG. 12H). In total, these results suggest that PEG-OACs can improve the flow of electrons to Complex IV and that the DS cells are more sensitive to this effect than the AHI cell lines. The dramatic increase in maximal respiration in the DS cells with PEG-OAC treatment could reflect pent-up capacity due to compensatory increase in Complex IV, reported to occur in mitochondria from DS individuals.

Mitochondrial respiration is assessed using the MitoStress Agilent Seahorse XFe96 (IBT Metabolomics Core; Feng Wang, PhD, Director) to measure changes in maxima and spare and mitochondrial ATP production using oxygen consumption rate (OCR) (FIG. 12A) of AHI and DS lymphocytes. A glycolytic rate test is used to measure changes in glycolysis, a measure of mitochondrial inhibition in this context by measuring extracellular acidification, an indicator of lactate production (52, 54, 55).

Figure 12D:
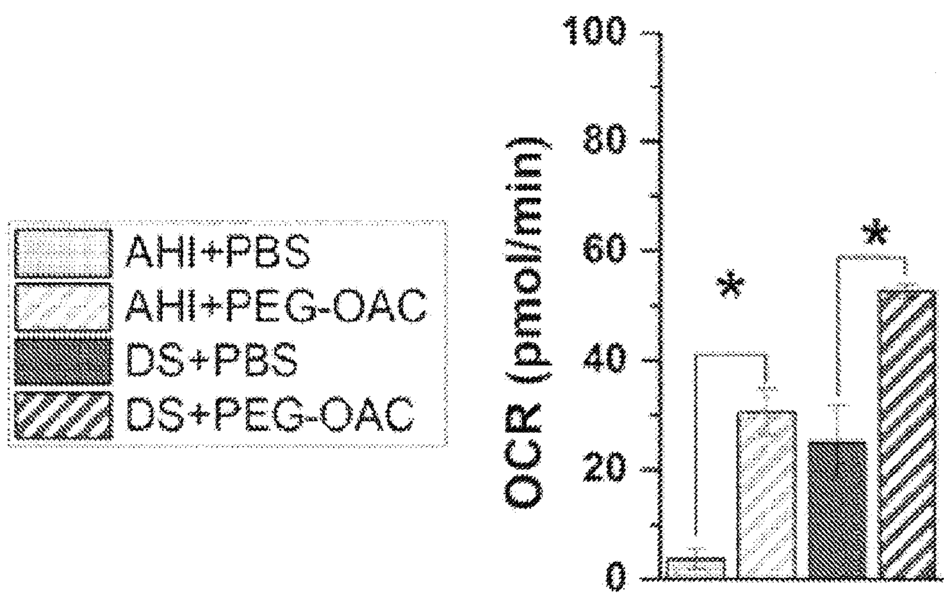
Figure 12E:
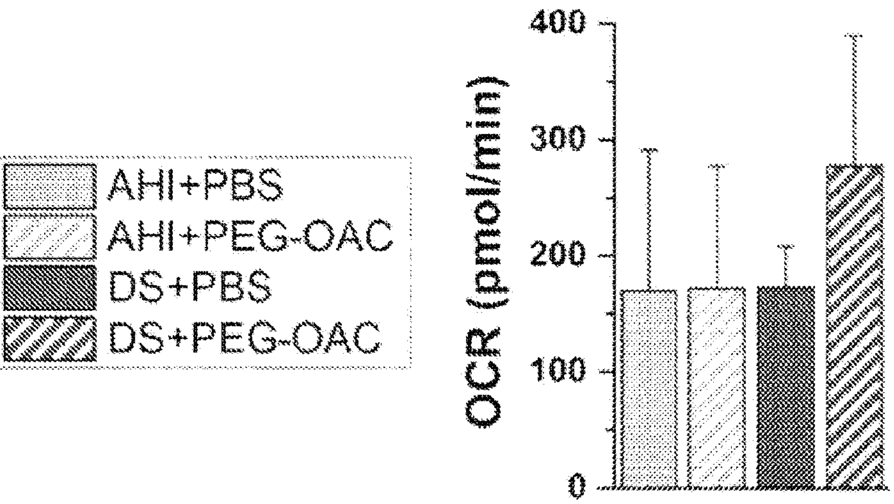
Figure 12F:
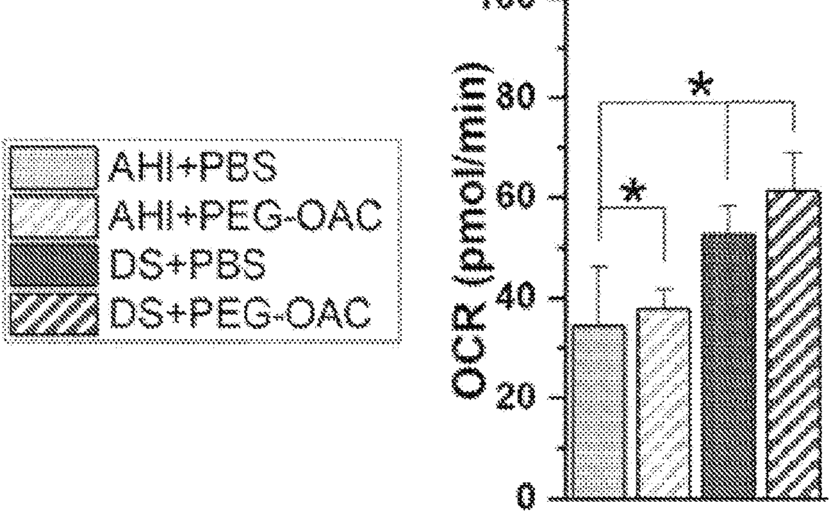
Figure 12G:
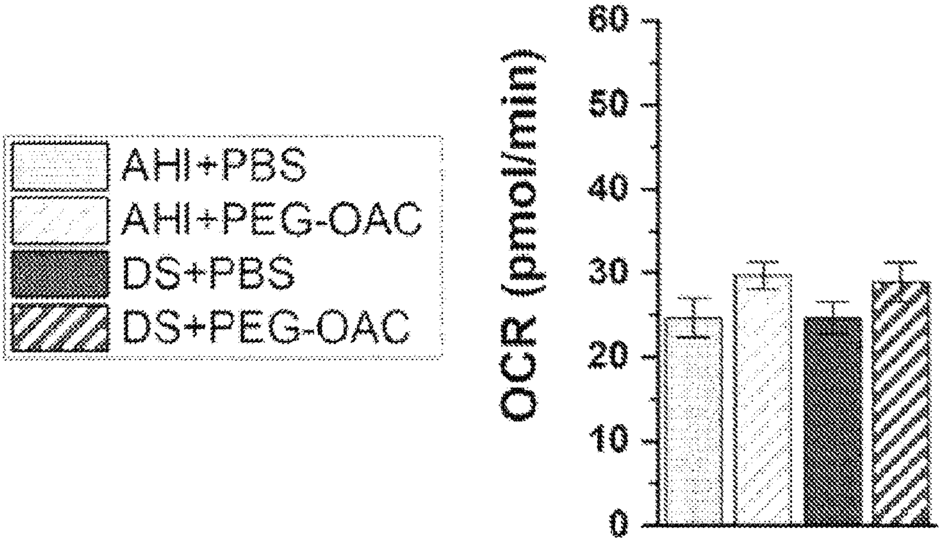
Figure 12H:
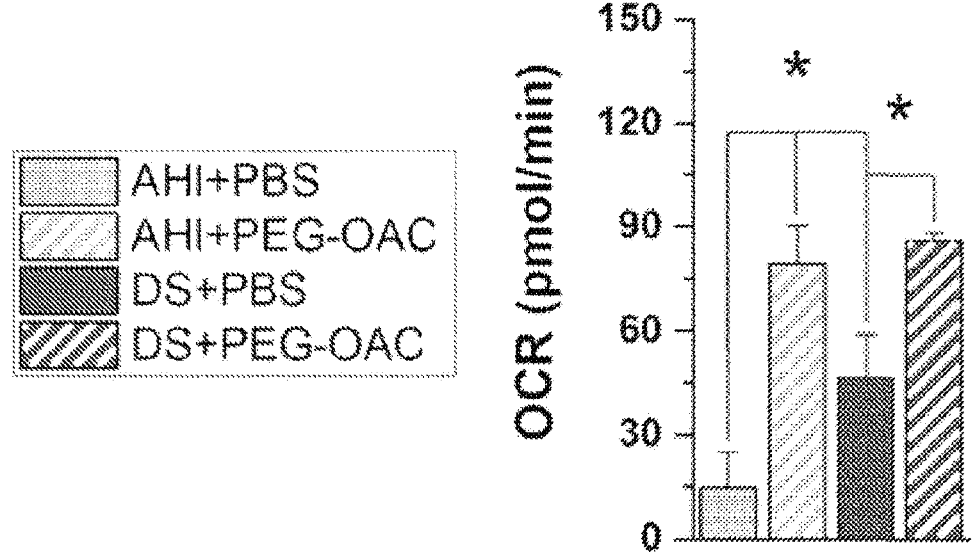

The results of this study showed that PEG-OACs increased the basal respiration rate (FIG. 12B) in DS cells treated with PEG-OACs, reduced proton leak (FIG. 12C), increased mitochondrial ATP synthesis (FIG. 12D). On average there was an increase in maximal respiration (FIG. 12E) when DS cells were treated with PEG-OACs with concomitant increase in spare respiratory capacity (FIG. 12F). Nonmitochondrial respiration was not significantly affected regardless of treatment (FIG. 12G). Coupling efficiency increased in both AHI and DS donor cells (FIG. 12H).

Oxidative stress is evaluated using CellROX® and MitoSOX™ fluorescence assays. These studies provide the necessary in vitro data to translate to in vivo dosage based on vascular volume as we have successfully done in the past (21, 22, 48).

The results from this study provide evidence that a catalytic nanoparticle can enhance the conversion of $H_2S$ and improve multiple parameters of health of cells containing DS mutation, therefore potentially have beneficial systemic effects in vivo.

In this study, we compared the effects of OCNPs on both DS and AHI cells with untreated cells as controls for each cell type. To compare the two groups, we perform a two-way ANOVA analysis with post-hoc Freeman-Tukey analysis. We performed each study at least 6 times for sufficient power to determine significance. Cell counting assesses whether proliferation is significantly reduced, suggesting toxicity.

Detrimental effects of $H_2S$ excess may not be apparent in cultured DS-donor cells but may be apparent if those cells are stressed by sub-lethal mitochondrial toxins. To test this possibility, we examine PEG-OACs protection of DS-donor cells against antimycin A (AMA), an electron transport chain inhibitor, and hydrogen peroxide, a general oxidative stress inducer.

Figure 8:
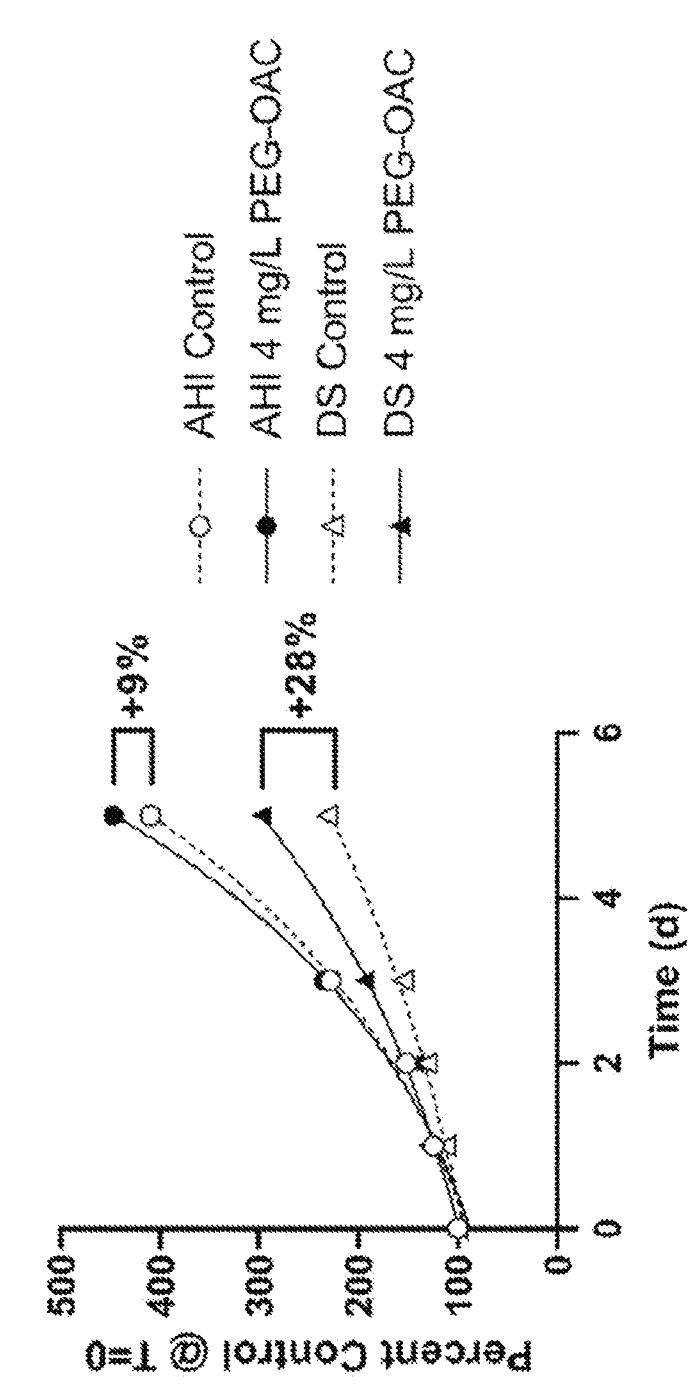
FIG. 8 is a plot of cellular proliferation of Down Syndrome (DS) and apparently healthy individual donor lymphocytes (AHI) treated with and without 4 mg/L PEG-OACs. The plot indicates that the difference in the proliferation with the AHI donor cells is +9% whereas the DS lymphocytes grew +28% faster.

Another study, whose results are shown graphically in FIG. 8, utilized lymphocytes from DS patients and those from apparently healthy individuals (AHI). In that study, cellular doubling times were determined, and it was found that AHI lymphocytes doubled their numbers almost twice as rapidly as lymphocytes from DS patients. After administration of increasing concentrations of PEG-OACs, it was found that the doubling time for the DS lymphocytes dose-dependently decreased by about 20% compared to about 8% for the AHI lymphocytes when measured at a concentration of 4 mg/L.

The rates of proliferation of both cell types was compared in the presence and absence of 4 mg/L PEG-OACs. As is seen from the results shown in FIG. 8, over the five-day study time the rate of proliferation of the AHI lymphocytes increased about 9% in the presence of the PEG-OACs, whereas the proliferation of the DS lymphocytes in the presence of the 4 mg/L PEG-OACs increased by about 28% over those grown in the absence of PEG-OACs (FIG. 8).

As shown in these studies, lymphocytes from DS patients manifest a lower proliferation rate than matched control lymphocytes at baseline. This could represent energy metabolism dysfunction secondary to excess $H_2S$. PEG-OACs had much less effect on control's lymphocyte proliferation. PEG-OACs dose-dependently increased lymphocyte proliferation at concentrations like those shown to be effective in animal models of brain injury.

DS and AHI lymphocytes were passed at an initial concentration of 10,000 cells/mL in 1.5 mL aliquots of Complete Media into a 12-well cell culture treated plate. The cells were treated with 0, 0.5, 1, 4, and 8 mg/L PEG-OACs. After 24 hours after seeding the plate, the lymphocytes were resuspended and 100 μL were removed for counting on an eight-quadrant hemocytometer and counted by microscope. Counting was repeated at 48, 72, and 120 hrs. Growth rates were calculated using Graphpad 9.1 (GraphPad Software, San Diego, CA).

Donor Epstein-Barr Virus immortalized DS and AHI lymphocytes (GM01921 (23, M) and GM07491 (17, M), respectively) were purchased from the Coriell Institute (Camden, NJ) under a materials transfer agreement with Texas A&M University and permissive to development of drugs or commercial products.

To determine the magnitude OCNPs on $H_2O_2$-produced ROS, we use MitoSOX™ (Thermo Fisher Scientific, Waltham, MA) labeling to estimate the antioxidant effect on mitochondrial superoxide, and lipid peroxidation screening using BODIPY, an indicator of the terminal products of ROS production. These findings are compared to those of AHI cells to determine if there are additional effects in the DS-donor cells. The prototype antioxidant Trolox is tested alone and in combination to differentiate antioxidant effects of the OCNPs from their effects on $H_2S$ conversion given that Trolox [(±)-6-hydroxy-2,5,7,8-tetramethylchromane-2-carboxylic acid] has no catalytic action on generation of polysulfides.

Figure 11:
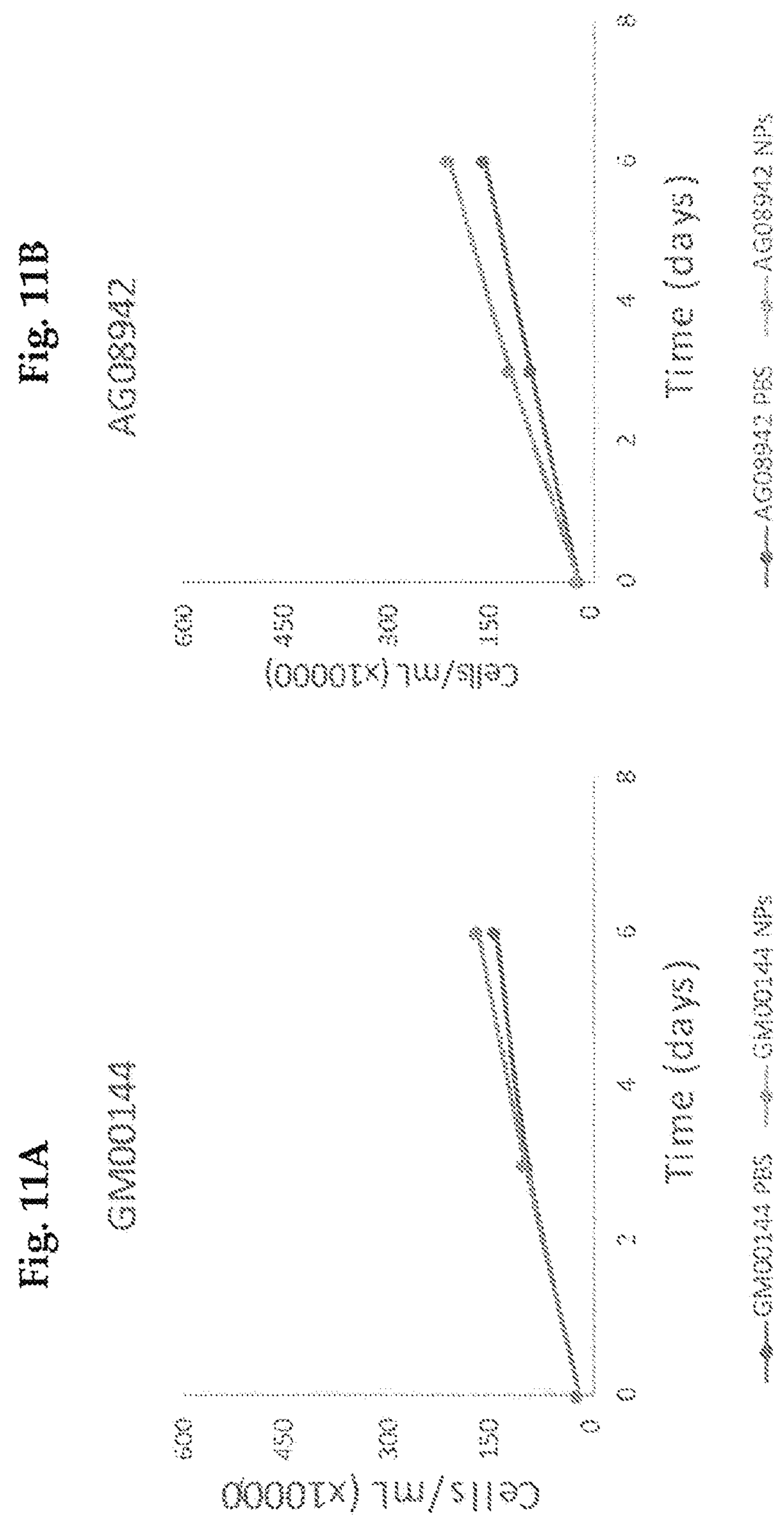
FIG. 11, in five panels as FIGS. 11A-11E, shows four plots of a particular DS cell line treated with PBS or 4 mg/L PEG-OACs. All four show an increase proliferation rate when treated with PEG-OACs, but all four also have different growth dynamics and exemplify the necessity for comparing individual cell lines or stratification. Regardless, as shown in FIG. 11E, the PEG-OACs still increase the cell proliferation rate on average.
Figures 11C, 11D:
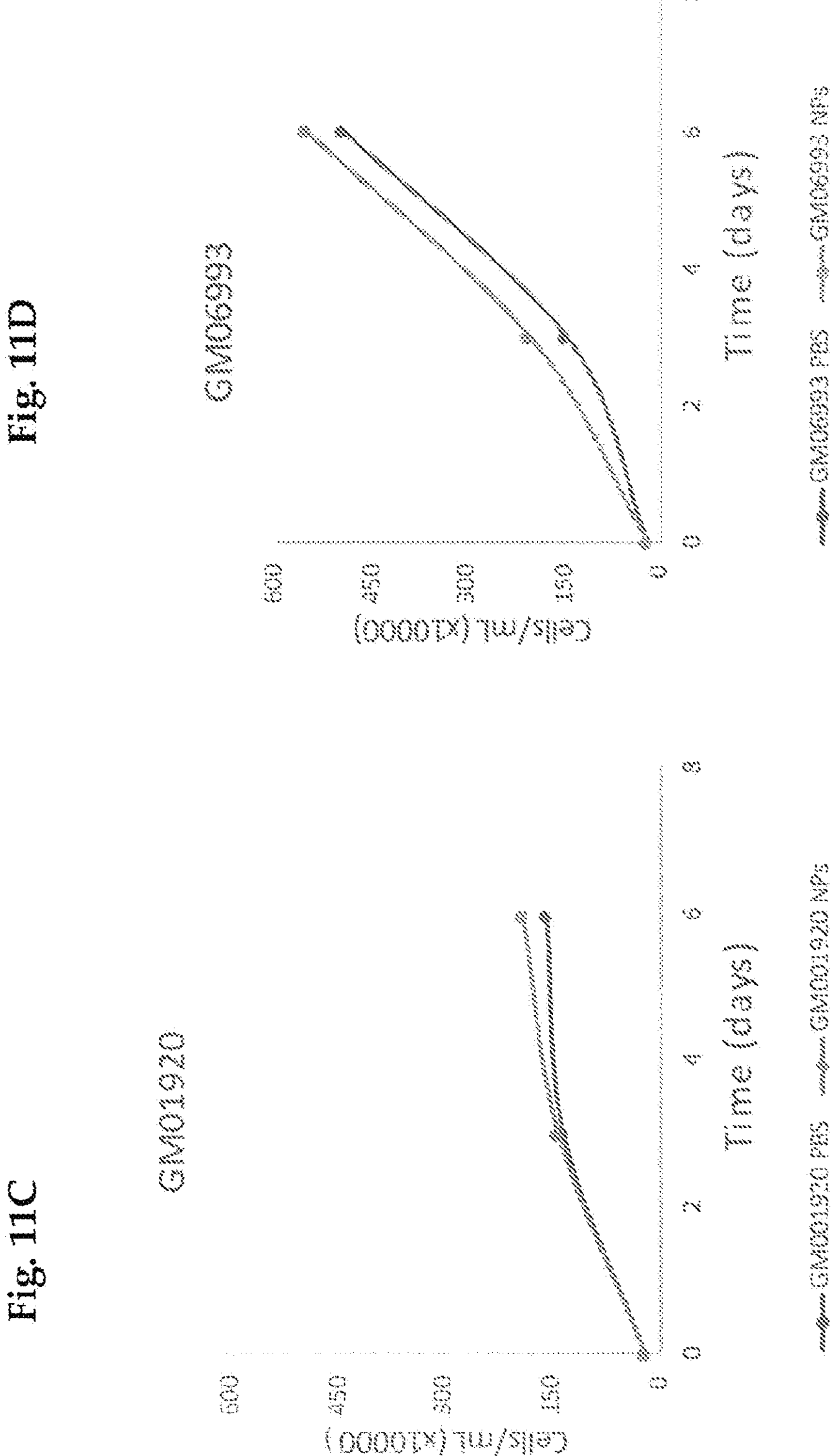
Figure 11E:
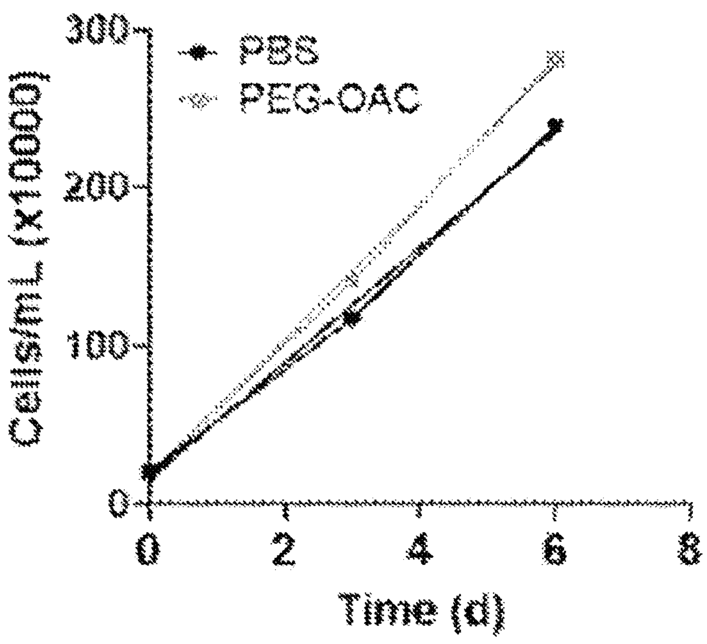

A major difficulty in obtaining narrow distributions of data is the wide variability of the replicative properties of the DS and AHI cells (FIGS. 11A, 11B, 11C, 11D). Despite that wide variability, we still observed a positive change in proliferation when treated with PEG-OACs (FIG. 11E).

Figures 9, 9A:
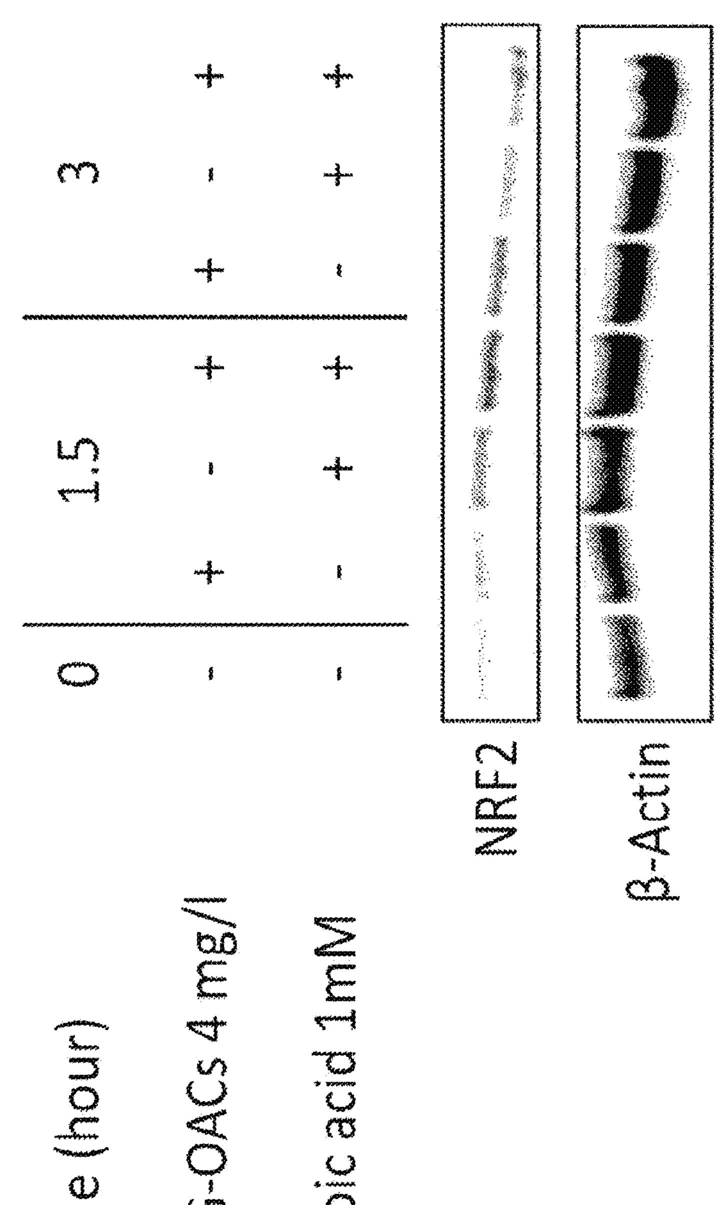
FIG. 9, in two panels as FIG. 9A and FIG. 9B, illustrate the synergistic effect of lipoic acid and PEG-OACs.
FIG. 9A is an image of an Anti-Nrf2 labeled Western blot showing the expression of Nrf2 in bEnd.3 cells that received PEG-OACs (EME28) 4 μg/ml and/or lipoic acid 1 mM. There is a strong potentiation of the Nrf2 levels with the combination of PEG-OACs and lipoic acid at 3 hours (arrow) with some small increases in signal from lipoic acid alone and the combination at 1.5 hours.
Figure 9B:
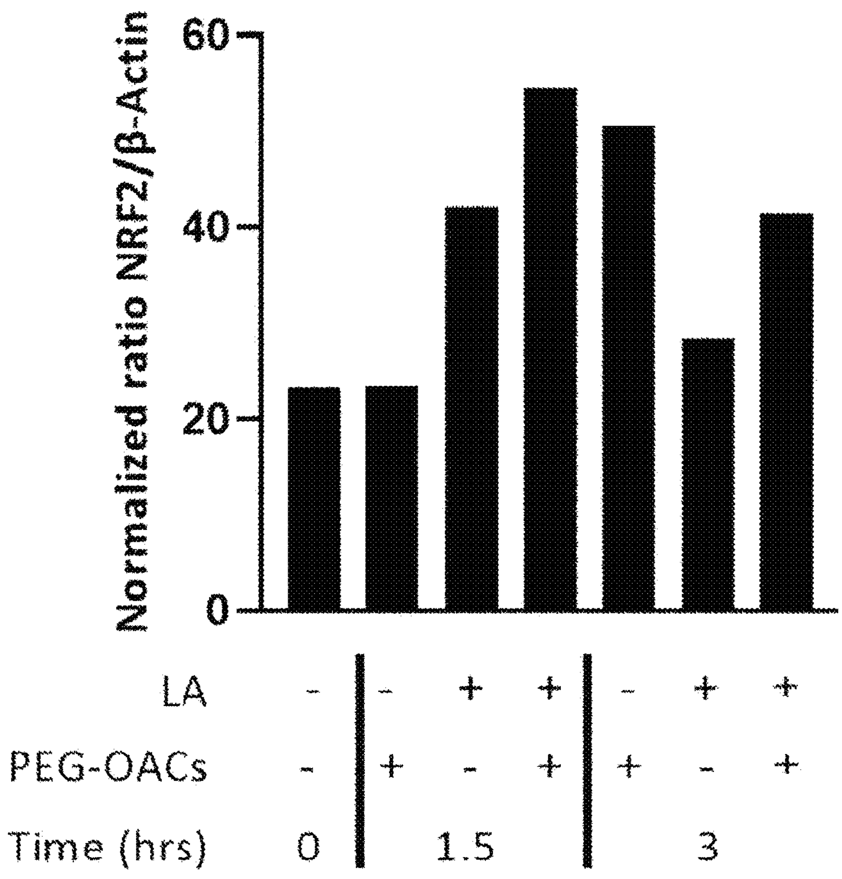
FIG. 9B illustrates quantification of band intensity relative to beta-actin control and shows the strong signal with the combination therapy. This synergistic effect was seen in 3/3 experiments, albeit at earlier or similar time points.

To determine the amount of free Nrf2, we performed SDS-PAGE electrophoresis followed by Western blotting using a Nrf2 specific antibody (FIGS. 9A, 9B). We combinatorically treated the cells with PEG-OACs (4 mg/L) and lipoic acid (1 mM) or PBS and collected samples for analysis at 1.5 and 3 hours (FIG. 10B).

We found that PEG-OACs increased Nrf2 expression by approximately 100% when PEG-OACs are combined with lipoic acid, in this example, at three hours following treatment. The lipoic acid is thus present in a potentiating amount such as about 0.1 to about 5 mM, and preferably at about 0.5 to about 3 mM.

To imbue PEG-OACs with additional functionality, dihydrolipoic acid, lipoic acid, or their analogs can be conjugated directly to the PEG-OACs or through a linker molecule. Lipoic acid and dihydrolipoic acid are chiral and use of the R enantiomer is preferred. Thus, lipoic acid or dihydrolipoic acid carboxyl group can be esterified to the hydroxyl groups of a contemplated particle using standard esterification techniques. The lipoic acid carboxyl group can be formed into an aminoalkylamide as by reaction with an alpha,omega-$C_2$-$C_6$-alkyldiamine whose amine group can then be reacted with a particle's keto of carboxy functionality.

Dihydrolipoic acid is immediately active and can improve intracellular glutathione levels as has been shown with free dihydrolipoic acid previously (56). Lipoic acid can itself act as a scavenger of $H_2S$ through the nucleophilic attack of HS— on to the dithiolane ring to produce a persulfide and thiol.

However, attack by HSS— can produce a persulfide R—SSSH that serves as a good electrophile for nucleophilic attack by glutathione and the production of highly reactive glutathione molecules. $H_2S$ has been shown in this application to be oxidized by PEG-OACs to polysulfides. Activation of the lipoic acid moieties by polysulfide can help enhance the reactivity of endogenous glutathione by increasing the concentration of glutathione persulfides.

It is contemplated that in addition to iron chelation, other metals can be chelated using sulfur-containing thiolane and thiol molecules with facile conjugation to the OCNP via amide coupling or 'click', azido-alkyne coupling, chemistry (FIG. 14). Such ligands include: 3-amino-1,2-propanedithiol, 4-amino-1,2-butanedithiol, 5-amino-1,2-pentanedithiol, 6-amino-1,2-hexanedithiol, 1-amino-2,3-butanedithiol, 2-(aminomethyl)-1,3-propanedithiol, α-lipoic acid, 1,2-dithiolane-3-pentamine and their respective salts. 3-(5-Hexyn-1-yl)-1,2-dithiolane, 3-(7-1-octyn-1-yl)-1,2-dithiolane, 3-(6-heptyn-1-yl)-1,2-dithiolane, 3-(1-methyl-4-pentyn-1-yl)-1,2-dithiolane, 3-(5-methyl-6-heptyn-1-yl)-1,2- dithiolane and other examples with poly(ethylene glycol) tails terminated by alkynes of various lengths are examples of azido-alkyne ("Click Chemistry") coupling derivatives.

The polymer modification of OCNPs using different blends of omega-methoxy-poly(ethylene glycol) amine has been performed by our group with physical demonstrations of 2,000+5,000 molecular weight PEG-$NH_2$ blends, and individually: 1,000, 2,000, 5,000, and 10,000 molecular weight PEG. Use of 5,000 Da PEG is presently preferred.

Because of the facile coupling of PEG-$NH_2$ to OCNPs using DIC coupling (FIG. 6), other amine-terminated polymers can also be suitable for coupling and can imbue new properties such as conditional solubility by acidity, attachment of a fluorescent moiety, or cell signalling molecule.

By coupling the ligand to the OCNP we aim to achieve two ends: 1) the thiol can serve as an additional antioxidant, 2) the thiol or thiolane interacts with the molecular orbitals of the OCNP to add additional catalytic activity to the OCNP.

Methods of Treatment and Pharmaceutical Compositions

A method of treating accelerated aging in a subject (patient) with Down syndrome (DS) is contemplated. That method contemplates contacting the subject's cells with an accelerated aging-relieving effective amount of hydrophilic polymer-functionalized oxidized carbon nanoparticles (OCNPs) as described herein such as the illustrative poly(ethylene glycol)-functionalized oxidized activated charcoal (PEG-OACs) used herein.

In accordance with use of a contemplated method, and shown by the results of FIG. 12, one or more of the following improvements in cell condition can occur and be monitored after administration of contemplated OCNPs: basal oxygen consumption rate (OCR) in DS donor lymphocytes was higher than those of the AHI donor lymphocytes and both the AHI and DS donor lymphocytes increased OCR when contacted by PEG-OACs to a somewhat greater extent in the DS cells; the amount of OCR associated with protons returning to the matrix without driving Complex V, of AHI and DS donor lymphocytes were reduced by the PEG-OACs, showing a marked decrease in proton leak; maximal respiration and spare respiratory capacity were dramatically increased in the PEG-OAC treated DS cells.

The oxidized carbon nanomaterials also provide for minimal toxicity to the subject being treated.

A contemplated OCNP can be used in the manufacture of a medicament (pharmaceutical composition) that is useful in a contemplated method of treatment. When so used, pharmaceutically acceptable salts, buffers and the like are typically present that collectively are referred to as pharmaceutically acceptable diluents as compared to those that can be present in a composition that is not intended for pharmaceutical use.

Without further syntheses, a contemplated oxidized carbon nanoparticulate material is present as a carboxylic acid and/or carboxylate anion. A cation such as monovalent lithium, sodium, potassium, and ammonium ions, or a divalent ion such as magnesium or calcium can be present to balance the charge of a carboxylate group.

Amine-containing compounds can also be associated with the contemplated particles, either linked covalently or non-covalently or merely bound by hydrophobic or hydrophilic or other forces. A solubilizing agent such as poly(ethyleneimine) (PEI) is associated with the particles, it is likely that the number of positive charges from that polymer's protonated amine groups will outnumber the negative charges of the particles' carboxylates at the usually near neutral pH value of most bodily fluids [at physiological pH values (about 7.2-7.4)] or cell culture media contemplated. Anionic groups can therefore be present to balance the positive charges.

Illustrative useful anions include but are not limited to the following: sulfate, hydrochloride, hydro bromides, acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenyl-propionate, picrate, pivalate, propionate, succinate, tartrate, thiocyanate, tosylate, mesylate and undecanoate.

The reader is directed to Berge, *J. Pharm. Sci.* 1977 68(1):1-19 for lists of commonly used pharmaceutically acceptable acids and bases that form pharmaceutically acceptable salts with pharmaceutical compounds.

A contemplated pharmaceutical composition contains an accelerated aging-relieving effective amount of contemplated oxidized carbon nanoparticulate material or a pharmaceutically acceptable salt thereof dissolved or dispersed in a physiologically (pharmaceutically) acceptable carrier. Such a composition can be administered to mammalian cells in vitro as in a cell culture to contact those cells, or the cells can be contacted in vivo as in a living, host mammal in need such as a person with Down syndrome.

The data for the Figs. show that concentrations of about 0.1 to about 10 mg/kg of the recipient, host mammal's weight. Preferably, that concentration is about 0.5 to about 6 mg/kg, and more preferably about 2 mg/kg provide effective amounts in the present studies. Skilled workers can readily utilize those amounts to find an effective amount for a particular treated subject or cells to be treated.

A contemplated composition is typically administered in vivo to a subject in need thereof a plurality of times within one month, such as weekly, and can be administered over a period of several months to several years, to a lifetime. Down syndrome being a genetic disorder, a lifetime of treatment is expected.

A contemplated pharmaceutical composition can be administered orally (perorally) as a liquid or solid formulation. Administration parenterally, which is preferred, is carried out using a liquid pharmaceutical composition. In either situation, a formulation containing conventional nontoxic pharmaceutically acceptable carriers, adjuvants, and vehicles as desired.

The term parenteral as used herein includes subcutaneous injections, intravenous (which is most preferred), intramuscular, intraperitoneal, intrasternal injection, or infusion techniques. Formulation of drugs for oral and parenteral administration is discussed in, for example, Hoover, John E., *Remington's Pharmaceutical Sciences*, Mack Publishing Co., Easton, Pennsylvania; 1975 and Liberman, H. A. and Lachman, L., Eds., *Pharmaceutical Dosage Forms*, Marcel Decker, New York, N.Y., 1980.

Hydrophilic carbon clusters (HCCs), as discussed in citations (50, 51) and U.S. Patent publication 2020/0222453, are prepared from carbon nanotubes rather than powdered charcoal by similar chemistry to that used here. HCCs have been found to have a half-life in nude mice of about 2 to about 3 hours. Similar half-lives are expected here.

Solid dosage forms for oral administration can include capsules, tablets, pills, powders, and granules. The amount of a contemplated compound in a solid dosage form is an effective amount as discussed previously; and thus provides a concentration to the blood stream of about 0.1 to about 10 mg/kg, preferably about 0.5 to about 6 mg/kg, and more preferably about 2 mg/kg. A solid dosage form can be and usually is administered a plurality of times during a one-week time period.

In such solid dosage forms, a compound of this invention is ordinarily combined with one or more diluents appropriate to the indicated route of administration. If administered per os, the compounds can be admixed with lactose, sucrose, starch powder, cellulose esters of alkanoic acids, carboxycellulose, carboxycellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration.

Solid dosage forms such as capsules or tablets can contain a controlled-release formulation as can be provided in a dispersion of contemplated oxidized carbon nanoparticulate material active agent in hydroxypropylmethyl cellulose. In the case of capsules, tablets, and pills, the dosage forms can also include buffering agents such as sodium citrate, magnesium or calcium carbonate or bicarbonate. Tablets and pills can additionally be prepared with enteric coatings for passage through the stomach without release of the contemplated oxidized carbon nanoparticulate material.

A contemplated pharmaceutical composition is preferably adapted for parenteral administration. Thus, a pharmaceutical composition is preferably in liquid form when administered, and most preferably, the liquid is an aqueous liquid, although other liquids are contemplated as discussed below, and a presently most preferred composition is an injectable preparation.

Thus, injectable preparations, for example, sterile injectable aqueous or oleaginous solutions or suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that can be employed are water, Ringer's solution, and isotonic sodium chloride solution, phosphate-buffered saline. Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Other liquid pharmaceutical compositions include, for example, solutions suitable for parenteral administration. Sterile water solutions of the oxidized-carbon nanoparticles active component or sterile solution of the active component in solvents comprising water, ethanol, or propylene glycol are examples of liquid compositions suitable for parenteral administration. In some aspects, a contemplated oxidized-carbon nanoparticle material is provided as a dry powder that is to be dissolved (dispersed) in an appropriate liquid medium such as sodium chloride for injection prior to use.

It is also to be understood that in therapeutic formulations the active oxidized carbon nanoparticulate materials can be dispersed, dissolved, emulsified, suspended, lyophilized, encapsulated, micronized, nanoparticulated and the like. In addition, the formulations can contain solvents such as alcohols, polyols, esters, water; thickening and consistency modulating agents such as galactomannan gums, carbohydrate polymers such as starch, cellulose derivatives, alginic acid and derivatives, alkyl acrylate polymers and copolymers, polyvinyl alcohol and derivatives; film forming agents such as cellulose ethers, carbomers; chelating agents, emulsifying agents such as long chain fatty acids, regular or fatty alcohols, and or esters; amino acids, and buffering agents.

A stable lyophilized pharmaceutical composition as contemplated herein can be made by lyophilizing a solution comprising oxidized carbon nanoparticulate material alone or admixed with a bulking agent, e.g., mannitol, trehalose, raffinose, and sucrose or mixtures thereof. There are many other conventional lyophilizing agents. Among the sugars, lactose is the most common. Also used are citric acid, sodium carbonate, EDTA, benzyl alcohol, glycine, sodium chloride, etc. [See for example, Baheti et al., (2010) *J Excip Food Chem* 1(1): 41-54.]

In addition, sterile, fixed oils are conventionally employed as a solvent or suspending medium. For this purpose, any bland, sterile fixed oil can be employed including synthetic mono- or diglycerides. In addition, fatty acids such as oleic acid find use in the preparation of an injectable composition. Dimethyl acetamide, surfactants including ionic and non-ionic detergents, polyethylene glycols can be used. Mixtures of solvents and wetting agents such as those discussed above are also useful.

A mammal in need of treatment (a subject) and to which a pharmaceutical composition containing a contemplated compound is administered is typically a human. Other primates such as an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like can also be used as test subjects in toxicity assays and the like, but do not get Down syndrome and are therefore not usually considered subjects for treatment. Several rodent models that are trisomic for different sets of Hsa21 genes have been developed and can be test subjects. (See, N. Rueda, J. Florez and C. Martinez-Cue, Mouse Models OF Down Syndrome as a Tool to Unravel the Causes of Mental Disabilities, *Neural Plast*, (2012) Article ID 584071, 26 pages doi: 10.1155/2012/584071; Y. Herault, J. M. Delabar, E. M. C. Fisher, V. L. J. Tybulewicz, E. Yu and V. Brault, Rodent models in Down syndrome research: impact and future opportunities, (2017) *Dis. Models Mech* 10:1165-1186 doi: 10.1242/dmm.029728.)

Where an in vitro assay is contemplated, a sample to be assayed such as cells and tissue can be used. These in vitro compositions typically contain the water, sodium or potassium chloride, and one or more buffer salts such as and acetate and phosphate salts, Hepes or the like, a metal ion chelator such as EDTA that are buffered to a desired pH value such as pH 4.0-8.5, preferably about pH 7.2-7.4, depending on the assay to be performed, as is well known.

Preferably, a pharmaceutical composition is in unit dosage form. In such form, the composition is divided into unit doses containing appropriate quantities of the oxidized carbon nanoparticulate material active compound. The unit dosage form can be a packaged preparation, the package containing discrete quantities of the preparation, for example, in vials or ampules.

General Methods

Oxidation of Activated Charcoal—Powdered medical grade coconut activated charcoal (cAC) (2.500 g, 208.3 mmol carbon) was added to a 250 mL round-bottom flask, followed by the addition of fuming (90%) $HNO_3$ (25 mL, 0.6 mol). The reaction mixture was placed in an oil bath pre-heated to 140° C. and stirred under reflux for 4 hours (h).

After heating, the reaction mixture was removed from the heat source and permitted to cool to room temperature.

The round-bottom flask containing the reaction mixture was then placed in an ice bath to chill before pouring into a 2 M aqueous glycine solution (25 mL, 50 mmol). The resulting quenched solution was transferred to one Spectra/Por® 7 dialysis membrane (regenerated cellulose, 1 kDa MWCO, 5 cm×45 mm dimensions) for purification by dynamic bath dialysis with deionized water (DI) water. The resulting cOAC solution was purified via the bath dialysis for 24 h.

After purification, the reaction mixture was removed from the dialysis bath and filtered through a 0.22 μm PES membrane. UV-vis spectrophotometry was used to determine the concentration of the aqueous cOAC product.

For the sieved cAC-derived cOAC, <20 μm powdered medical grade cAC was collected by sieving the bulk cAC (3.0 g, 0.25 mol carbon) through a U.S.A. standard test sieve with No. 635 (20 μm) openings prior to oxidation. To aid the sieving process, a Gilson vibratory sieve shaker was used (parameters: mode=manual, time=2 h, amplitude=100%). The collected <20 μm cAC was subsequently oxidized by the above method.

Functionalization of Improved cOAC with PEG—Aqueous cOAC was dried by lyophilization (Labconco™ Freeze Dry System/Freezone 4.5). The lyophilized bulk- or sieved-cOAC (16.6 mg, 1.38 mmol) was suspended in DMF (10 mL) and cup horn sonicated for 60 min at 50% amplitude (Cole-Parmer® Ultrasonic Processor CP 750).

Then 5 kDa methoxy-PEG-amine (0.3327 g, 0.06654 mmol) was added to the reaction vessel. The mixture was bath-sonicated for 20 minutes (min) (Cole-Parmer® 08849-00 ultrasonic cleaner). Next, the reaction vessel was removed from the sonicator and N,N'-diisopropylcarbodiimide (DIC) (0.17 mL, 1.1 mmol) was added. The solution was stirred for 48 h at room temperature (rt). Prior to purification by bath dialysis, excess DMF was removed by centrifugation (NuAire® NU-C200R, parameters: 4500× g, 30 min, room temperature) using Amicon® Ultra-15 Centrifugal Filters (regenerated cellulose, 10 kDa MWCO).

The resulting retentate was diluted in Milli-Q® water and then transferred to one Float-A-Lyzer® G2 dialysis device (regenerated cellulose, MWCO 50 kDa, 10 mL volume capacity). To dialyze the material, the filled device was placed in a 2 L beaker containing Milli-Q Water®. During a period of 48 h, the water bath was slowly and continuously stirred by a magnetic stir bar/stir plate. The water was exchanged 6-8 times over the course of this time.

After dialysis, the PEG-cOAC particles were sterile-filtered by passing through a 0.22 μm polyethersulfone (PES) membrane. UV-vis spectrophotometry was used to determine the cOAC carbon core concentration of the resulting aqueous PEG-cOAC product.

SSP4 Fluorescence Assay—A solution of 1200 μM Na2S in PBS was prepared and used freshly. A 120 μM solution of SSP4 was prepared in PBS and kept wrapped in foil. In a 96-well plate, 50 μL of 16 μg/mL PEG-OACs or PBS followed by 50 μL of the SSP4 solution, 50 μL of PBS, and finally 50 μL of the 1200 μM $Na_2S$ solution was added to the plate in two wells. Using a BMG Clariostar operating in fluorescence mode, the two wells were scanned once every 10 seconds for 600 seconds.

Proliferation Assay—DS and AHI fibroblasts are treated with 0.1-10 mg/L PEG-OAC based on our experience. Treatment times will vary from 1-5 days. Two-way ANOVA determines if the PEG-OACs enhance proliferation using particle concentration X cell genotype to determine which gives the largest protective effect.

Intracellular Polysulfide Assay—HEK293 cells were treated with 1, 3, or 9 μg/mL PEG-OACs for four days and were incubated with 30 μM of SSP4, the plate was read periodically and a progress curve obtained.

Thiosulfate Production Assay—DS and AHI fibroblasts are prepared in culture and incubated with and without PEG-OACs (0-9 μg/mL). The concentration of thiosulfate is measured using Ag nanoparticles (AgNPs) as previously described (30). A thiosulfate calibration curve with the AgNPs is collected using a HP 8453 UV-vis spectrophotometer using the absorbance at 419 nm as the collection point. Aliquots of the media are collected every day and added to a solution of the nanoparticles to measure the reduction in the absorbance at 419 nm.

Mitochondrial Respirometry—DS and AHI-donor cells are cultured and treated with OCNPs (0.1-10 mg/L) and/or Trolox (1-100 μM) prior to placement in a Seahorse XFe96 mitochondrial respiration and glycolysis analyzer (Agilent Technologies Inc., Wood Dale, IL) after which a full dose mitochondrial stress test was performed using sequential treatment of oligomycin, carbonyl cyanide-p-trifluoromethoxy-phenylhydrazone (FCCP), and rotenone/antimycin A. The difference in OCR following treatment with each drug for the treated and untreated groups are compared using the procedure described by Agilent Technologies (54).

In a second study, cells with and without OCNP and Trolox are treated with either antimycin A or hydrogen peroxide; the percent difference in OCR between the treated and untreated cells is analyzed. We perform a glycolytic rate test to measure changes in compensatory glycolysis, or the ability for cells to respond to a loss in the electron transport chain. A reduction in this factor indicates weaker inhibition of the mitochondria (52. 55).

Culture of bEnd.3 Cells for Nrf2 Study—Mouse brain endothelial (b.End3) cells are grown and maintained in DMEM supplemented with 10% fetal bovine serum and 1% penicillin streptomycin. Once cells reach 90% confluence, cells are split in a 1-to-5 ratio.

Treatment of bEnd.3 Cells for Nrf2 Study—b.End3 cells are seeded on 10-cm petri dishes. On day 4, half of the old media is discarded and replaced with fresh media. On day 5, b.End3 cells receive either PEG-OACs (EME28) 4 μg/ml or lipoic acid 1 mM or vehicle (PBS).

Nrf2 Western blotting—Cell extraction is performed using Cell Lysis Buffer and the provided protocol (ThermoFisher #FNN0011). Proteins are quantified using Bradford assay (Thermofisher #1863028). Same amounts of proteins of each lysate (20 μg) are loaded on an SDS-PAGE gel under reducing conditions (unless stated otherwise). Membrane transfer is done overnight (about 18 hours) in cold room and blocked with 5% dry milk/TBST the next day. Subsequently, the membrane is incubated with primary antibodies overnight (about 18 hours) and with secondary antibodies for an hour in blocking solution. Signals are developed with ECL (ThermoFisher #A43840) and captured with ChemiDoc™ Imaging System.

Anti-PEG Labeling of Sprague-Dawley Rat Brains—The brain from a Sprague-Dawley rat treated parentally with 2 mg/kg PEG-OAC was fixed in 4% formaldehyde on ice for 24 hours and cryoprotected using a concentration gradient from 10% to 30% sucrose in $H_2O$ over 48 hours. Afterwards, the brain was sectioned using a Leica cryotome in 20 um sections. The sections were labeled with an Anti-PEG Rb polyclonal antibody (Invitrogen #PA5-32247) followed by AlexaFluor 647-labeled goat anti-Rabbit IgG secondary antibody (Invitrogen #A-21245) and imaged using a Leica DMi 8 inverted fluorescence microscope at 20×.

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

CITATIONS

1. Gardiner, K., Costa, A. C. S., The Proteins of Human Chromosome 21, Am J Med Genet C Semin Med Genet. 142C(3) (2006) 196-205 PubMed PMID.
2. Kamalakar, A., Harris, J. R., McKelvey, K. D., Suva, L. J., Aneuploidy and skeletal health, Curr Osteoporos Rep 12(3) (2014) 376-82 PubMed PMID: PMC4136427.
3. Thomas, J. R., Roper, R. J., Current Analysis of Skeletal Phenotypes in Down Syndrome, Curr Osteoporos Rep 19(3) (2021) 338-346 PubMed PMID: PMC8316313.
4. Mai, C. T., Isenburg, J. L., Canfield, M. A., Meyer, R. E., Correa, A., Alverson, C. J., Lupo, P. J., Riehle-Colarusso, T., Cho, S. J., Aggarwal, D., Kirby, R. S., National population-based estimates for major birth defects, 2010-2014, Birth Defects Research 111(18) (2019) 1420-1435 PubMed PMID.
5. Shin, M., Besser, L. M., Kucik, J. E., Lu, C., Siffel, C., Correa, A., Congenital Anomaly Multistate, P., Survival, C., Prevalence of Down syndrome among children and adolescents in 10 regions of the United States, Pediatrics 124(6) (2009) 1565-71 PubMed PMID.
6. Gensous, N., Bacalini, M. G., Franceschi, C., Garagnani, P., Down syndrome, accelerated aging and immunosenescence, Semin Immunopathol 42(5) (2020) 635-645 PubMed PMID: PMC7666319.
7. Horvath, S., Garagnani, P., Bacalini, M. G., Pirazzini, C., Salvioli, S., Gentilini, D., Di Blasio, A. M., Giuliani, C., Tung, S., Vinters, H. V., Franceschi, C., Accelerated epigenetic aging in Down syndrome, Aging Cell 14(3) (2015) 491-5 PubMed PMID: PMC4406678.
8. Lott, I. T., Head, E., Dementia in Down syndrome: unique insights for Alzheimer disease research, Nat Rev Neurol 15(3) (2019) 135-147 PubMed PMID: PMC8061428.
9. Head, E., Powell, D., Gold, B. T., Schmitt, F. A., Alzheimer's Disease in Down Syndrome, Eur J Neurodegener Dis 1(3) (2014) 353-364 PubMed PMID: PMC4184282.
10. Ichinohe, A., Kanaumi, T., Takashima, S., Enokido, Y., Nagai, Y., Kimura, H., Cystathionine beta-synthase is enriched in the brains of Down's patients, Biochem Biophys Res Commun 338(3) (2005) 1547-50 PubMed PMID.
11. Kanaumi, T., Ichinohe, A., Kimura, H., Iwasaki, H., Hirose, S., Takashima, S., Development and Aging Expression of Cystathionine-Beta Synthase in the Temporal Lobe and Cerebellum of Down Syndrome Patients, Neuroembryol Aging 2006-07(4) (2008) 202-207 PubMed PMID.
12. Pogribna, M., Melnyk, S., Pogribny, I., Chango, A., Yi, P., James, S. J., Homocysteine metabolism in children with Down syndrome: in vitro modulation, Am J Hum Genet 69(1) (2001) 88-95 PubMed PMID: PMC1226051.
13. Marechal, D., Brault, V., Leon, A., Martin, D., Lopes Pereira, P., Loaec, N., Birling, M. C., Friocourt, G., Blondel, M., Herault, Y., Cbs overdosage is necessary and sufficient to induce cognitive phenotypes in mouse models of Down syndrome and interacts genetically with Dyrk1a, Hum Mol Genet 28(9) (2019) 1561-1577 PubMed PMID.
14. Szabo, C., The re-emerging pathophysiological role of the cystathionine-beta-synthase—hydrogen sulfide system in Down syndrome, FEBS J 287(15) (2020) 3150-3160 PubMed PMID.
15. Nandi, S. S., Mishra, P. K., $H_2S$ and homocysteine control a novel feedback regulation of cystathionine beta synthase and cystathionine gamma lyase in cardiomyocytes, Sci Rep 7(1) (2017) 3639 PubMed PMID: PMC5473925.
16. Panagaki, T., Randi, E. B., Augsburger, F., Szabo, C., Overproduction of $H_2S$, generated by CBS, inhibits mitochondrial Complex IV and suppresses oxidative phosphorylation in Down syndrome, Proc Natl Acad Sci USA 116(38) (2019) 18769-18771 PubMed PMID: PMC6754544.
17. Zis, P., McHugh, P., McQuillin, A., Pratico, D., Dickinson, M., Shende, S., Walker, Z., Strydom, A., Memory decline in Down syndrome and its relationship to iPF2alpha, a urinary marker of oxidative stress, PLOS One 9(6) (2014) e97709 PubMed PMID: PMC4046955.
18. Vacca, R. A., Bawari, S., Valenti, D., Tewari, D., Nabavi, S. F., Shirooie, S., Sah, A. N., Volpicella, M., Braidy, N., Nabavi, S. M., Down syndrome: Neurobiological alterations and therapeutic targets, Neurosci Biobehav Rev 98(2019) 234-255 PubMed PMID.
19. Sun, H.-J., Wu Z-Y, Nie, Z.-W., Bian, J.-S., Role of hydrogen sulfide and polysulfides in neurological diseases: focus on protein S-Persulfidation, Curr Neuropharmacol 19(6) (2020) 868-884 PubMed PMID.
20. Wu, G., McHugh, E. A., Berka, V., Chen, W., Wang, Z., Beckham, J. L., Derry, P. J., Roy, T., Kent, T. A., Tour, J. M., Tsai, A.-L., Oxidized Activated Charcoal Nanoparticles as Catalytic Superoxide Dismutase Mimetics: Evidence for Direct Participation of an Intrinsic Radical, ACS Applied Nano Materials 3(7) (2020) 6962-6971 PubMed PMID.
21. Mendoza, K., Derry, P. J., Cherian, L. M., Garcia, R., Nilewski, L., Goodman, J. C., Moye, L., Robertson, C. S., Tour, J. M., Kent, T. A., Functional and Structural Improvement with a Catalytic Carbon Nano-Antioxidant in Experimental Traumatic Brain Injury Complicated by Hypotension and Resuscitation, J Neurotrauma 36(13) (2019) 2139-2146 PubMed PMID: PMC6602099.
22. Bitner, B. R., Marcano, D. C., Berlin, J. M., Fabian, R. H., Cherian, L., Culver, J. C., Dickinson, M. E., Robertson, C. S., Pautler, R. G., Kent, T. A., Tour, J. M., Antioxidant carbon particles improve cerebrovascular dysfunction following traumatic brain injury, ACS Nano 6(9) (2012) 8007-14 PubMed PMID: PMC3458163.
23. Olson, K. R., Hydrogen sulfide, reactive sulfur species and coping with reactive oxygen species, Free Radic Biol Med 140(2019) 74-83 PubMed PMID.
24. Mishanina, T. V., Libiad, M., Banerjee, R., Biogenesis of reactive sulfur species for signaling by hydrogen sulfide oxidation pathways, Nat Chem Biol 11(7) (2015) 457-64 PubMed PMID: PMC4818113.
25. Yuan, S., Shen, X., Kevil, C. G., Beyond a Gasotransmitter: Hydrogen Sulfide and Polysulfide in Cardiovascular Health and Immune Response, Antioxid Redox Signal 27(10) (2017) 634-653 PubMed PMID: PMC5576200.
26. Moran, J., Hogan, H., Srsic-Stoehr, K., Service, K., Rowlett, S., Aging and Down Syndrome, National Down Syndrome Society, 2017, p. 39.

27. Vitvitsky, V., Banerjee, R., H2S analysis in biological samples using gas chromatography with sulfur chemiluminescence detection, Methods Enzymol 554(2015) 111-23 PubMed PMID: PMC4684085.

28. Reese, B. K., Finneran, D. W., Mills, H. J., Zhu, M.-X., Morse, J. W., Examination and Refinement of the Determination of Aqueous Hydrogen Sulfide by the Methylene Blue Method, Aquatic Geochemistry 17(4-5) (2011) 567-582 PubMed PMID.

29. Shen, X., Kolluru, G. K., Yuan, S., Kevil, C. G., Measurement of H2S in vivo and in vitro by the monobromobimane method, Methods Enzymol 554(2015) 31-45 PubMed PMID: PMC4413952.

30. Dong, C., Wang, Z., Zhang, Y., Ma, X., Iqbal, M. Z., Miao, L., Zhou, Z., Shen, Z., Wu, A., High-Performance Colorimetric Detection of Thiosulfate by Using Silver Nanoparticles for Smartphone-Based Analysis, ACS Sens 2(8) (2017) 1152-1159 PubMed PMID.

31. Sbodio, J. I., Snyder, S. H., Paul, B. D., Regulators of the transsulfuration pathway, Br J Pharmacol 176(4) (2019) 583-593 PubMed PMID: PMC6346075.

32. Wang, R., Physiological implications of hydrogen sulfide: a whiff exploration that blossomed, Physiol Rev 92(2) (2012) 791-896 PubMed PMID.

33. Jiang, J., Chan, A., Ali, S., Saha, A., Haushalter, K. J., Lam, W. L., Glasheen, M., Parker, J., Brenner, M., Mahon, S. B., Patel, H. H., Ambasudhan, R., Lipton, S. A., Pilz, R. B., Boss, G. R., Hydrogen Sulfide—Mechanisms of Toxicity and Development of an Antidote, Sci Rep 6(2016) 20831 PubMed PMID: PMC4753484.

34. Raghunath, A., Sundarraj, K., Nagarajan, R., Arfuso, F., Bian, J., Kumar, A. P., Sethi, G., Perumal, E., Antioxidant response elements: Discovery, classes, regulation and potential applications, Redox Biol 17(2018) 297-314 PubMed PMID: PMC6007815.

35. Yueh, M. F., Tukey, R. H., Nrf2-Keap1 signaling pathway regulates human UGT1A1 expression in vitro and in transgenic UGT1 mice, J Biol Chem 282(12) (2007) 8749-58 PubMed PMID.

36. Meijerman, I., Beijnen, J. H., Schellens, J. H., Combined action and regulation of phase II enzymes and multidrug resistance proteins in multidrug resistance in cancer, Cancer Treat Rev 34(6) (2008) 505-20 PubMed PMID.

37. Shen, G., Kong, A. N., Nrf2 plays an important role in coordinated regulation of Phase II drug metabolism enzymes and Phase III drug transporters, Biopharm Drug Dispos 30(7) (2009) 345-55 PubMed PMID: PMC2782863.

38. Molavian, H., Madani Tonekaboni, A., Kohandel, M., Sivaloganathan, S., The Synergetic Coupling among the Cellular Antioxidants Glutathione Peroxidase/Peroxiredoxin and Other Antioxidants and its Effect on the Concentration of H2O2, Scientific Reports 5(1) (2015) PubMed PMID.

39. Arteel, G. E., Briviba, K., Sies, H., Function of thioredoxin reductase as a peroxynitrite reductase using selenocystine or ebselen, Chemical res in toxicology 12(1999) 264-269 PubMed PMID.

40. Suzuki, T., Muramatsu, A., Saito, R., Iso, T., Shibata, T., Kuwata, K., Kawaguchi, S. I., Iwawaki, T., Adachi, S., Suda, H., Morita, M., Uchida, K., Baird, L., Yamamoto, M., Molecular Mechanism of Cellular Oxidative Stress Sensing by Keap1, Cell Rep 28(3) (2019) 746-758 e4 PubMed PMID.

41. Cuadrado, A., Rojo, A. I., Wells, G., Hayes, J. D., Cousin, S. P., Rumsey, W. L., Attucks, O. C., Franklin, S., Levonen, A. L., Kensler, T. W., Dinkova-Kostova, A. T., Therapeutic targeting of the NRF2 and KEAP1 partnership in chronic diseases, Nat Rev Drug Discov 18(4) (2019) 295-317 PubMed PMID.

42. Benchoam, D., Cuevasanta, E., Moller, M. N., Alvarez, B., Persulfides, at the crossroads between hydrogen sulfide and thiols, Essays Biochem 64(1) (2020) 155-168 PubMed PMID.

43. Olson, K. R., Briggs, A., Devireddy, M., Xian, M., Gao, Y., Are the beneficial effects of 'antioxidant' lipoic acid mediated through metabolism of reactive sulfur species?, Free Radic Biol Med 146 (2020) 139-149 PubMed PMID.

44. Perluigi, M., Butterfield, D. A., Oxidative Stress and Down Syndrome: A Route toward Alzheimer-Like Dementia, Curr Gerontol Geriatr Res 2012(2012) 724904 PubMed PMID: PMC3235450.

45. Di Domenico, F., Pupo, G., Mancuso, C., Barone, E., Paolini, F., Arena, A., Blarzino, C., Schmitt, F. A., Head, E., Butterfield, D. A., Perluigi, M., Bach1 overexpression in Down syndrome correlates with the alteration of the HO-1/BVR-a system: insights for transition to Alzheimer's disease, J Alzheimers Dis 44(4) (2015) 1107-20 PubMed PMID: PMC4677575.

46. Nilewski, L., Mendoza, K., Jalilov, A. S., Berka, V., Wu, G., Sikkema, W. K. A., Metzger, A., Ye, R., Zhang, R., Luong, D. X., Wang, T., McHugh, E., Derry, P. J., Samuel, E. L., Kent, T. A., Tsai, A. L., Tour, J. M., Highly Oxidized Graphene Quantum Dots from Coal as Efficient Antioxidants, ACS Appl Mater Interfaces 11(18) (2019) 16815-16821 PubMed PMID.

47. Samuel, E. L., Marcano, D. C., Berka, V., Bitner, B. R., Wu, G., Potter, A., Fabian, R. H., Pautler, R. G., Kent, T. A., Tsai, A. L., Tour, J. M., Highly efficient conversion of superoxide to oxygen using hydrophilic carbon clusters, Proc Natl Acad Sci USA 112(8) (2015) 2343-8 PubMed PMID: PMC4345556.

48. Derry, P. J., Nilewski, L. G., Sikkema, W. K. A., Mendoza, K., Jalilov, A., Berka, V., McHugh, E. A., Tsai, A. L., Tour, J. M., Kent, T. A., Catalytic oxidation and reduction reactions of hydrophilic carbon clusters with NADH and cytochrome C: features of an electron transport nanozyme, Nanoscale 11(22) (2019) 10791-10807 PubMed PMID.

49. Fabian, R. H., Derry, P. J., Rea, H. C., Dalmeida, W. V., Nilewski, L. G., Sikkema, W. K. A., Mandava, P., Tsai, A. L., Mendoza, K., Berka, V., Tour, J. M., Kent, T. A., Efficacy of Novel Carbon Nanoparticle Antioxidant Therapy in a Severe Model of Reversible Middle Cerebral Artery Stroke in Acutely Hyperglycemic Rats, Front Neurol 9(2018) 199 PubMed PMID: PMC5900022.

50. Dharmalingam, P., Talakatta, G., Mitra, J., Wang, H., Derry, P. J., Nilewski, L. G., McHugh, E. A., Fabian, R. H., Mendoza, K., Vasquez, V., Hegde, P. M., Kakadiaris, E., Roy, T., Boldogh, I., Hegde, V. L., Mitra, S., Tour, J. M., Kent, T. A., Hegde, M. L., Pervasive Genomic Damage in Experimental Intracerebral Hemorrhage: Therapeutic Potential of a Mechanistic-Based Carbon Nanoparticle, ACS Nano 14(3) (2020) 2827-2846 PubMed PMID: PMC7850811.

51. Tour, J. M., Nilewski, L., Sikkema, W. K., Mendoza, K., Kent, T. A., Dalmeida, W. V., Derry, P. J., Tsai, A. L., Hegde, M. L., Dharmalingam, P., Hegde, P. D., Mitra, S., Mitra, J., Acute and chronic mitochondrial electron transport chain dysfunction treatments and graphenic materials for use thereof, Rice University, United States of America, 2020.

52. Pecze, L., Szabo, C., Meta-analysis of gene expression patterns in Down syndrome highlights significant alterations in mitochondrial and bioenergetic pathways, Mitochondrion 57(2021) 163-172 PubMed PMID.

53. Asimakopoulou, A., Panopoulos, P., Chasapis, C. T., Coletta, C., Zhou, Z., Cirino, G., Giannis, A., Szabo, C., Spyroulias, G. A., Papapetropoulos, A., Selectivity of commonly used pharmacological inhibitors for cystathionine beta synthase (CBS) and cystathionine gamma lyase (CSE), Br J Pharmacol 169(4) (2013) 922-32 PubMed PMID: PMC3687671.

54. Technologies, A., Agilent Seahorse XF Cell Mito Stress Test Kit, 2019.

55. Technologies, A., Agilent Seahorse XF Glycolytic Rate Assay Kit, 2019.

56. Han, D., Handelman, G., Lipoic acid increases de novo synthesis of cellular glutathione by improving cystine utilization, Biofactors 6(3) (1997)

The invention claimed is:

1. A method for treating a Down syndrome (DS) subject presenting with functional decline of organ systems associated with accelerated aging due to over-production of $H_2S$ that comprises administering a pharmaceutical composition containing a $H_2S$-reducing effective amount of hydrophilic polymer-substituted oxidized carbon nanoparticles (OCNPs) dissolved or dispersed in a physiologically acceptable diluent to the subject.

2. The method according to claim 1, wherein said hydrophilic polymer substituent is free of ionic charge at physiologic pH values.

3. The method according to claim 2, wherein said hydrophilic polymer substituent is one or more of poly(ethylene glycol), poly(propylene glycol) or poly(ethylene glycol-co-propylene glycol).

4. The method according to claim 3, wherein said hydrophilic polymer substituent is poly(ethylene glycol) (PEG).

5. The method according to claim 4, wherein said substituent PEG has an average molecular weight of about 2000 to about 10,000 Da.

6. The method according to claim 4, wherein said OCNPs contain an average of about 3 to about 12 PEG substituents per particle.

7. The method according to claim 1, wherein said physiologically acceptable diluent is an aqueous liquid adapted for parenteral administration.

8. The method according to claim 7, wherein said aqueous liquid is Ringer's solution, isotonic sodium chloride solution or phosphate-buffered saline.

9. The method according to claim 7, wherein said hydrophilic polymer-substituted oxidized carbon nanoparticles are present at a concentration of about 0.1 to about 10 mg/kg.

10. The method according to claim 1, wherein said physiologically acceptable diluent is adapted for oral administration.

11. The method according to claim 10, wherein said physiologically acceptable diluent is an aqueous liquid.

12. The method according to claim 10, wherein said physiologically acceptable diluent is a solid.

13. The method according to claim 1, wherein said administration is repeated.

14. The method according to claim 1, wherein said administration is provided to a patient having an elevated level of $H_2S$.

15. The method according to claim 1, wherein the pharmaceutical composition further comprises lipoic acid, dihydrolipoic acid, or a combination thereof.

16. The method according to claim 15, wherein said lipoic acid is present at about 0.1 to about 5 mM.

17. A method for treating a Down syndrome (DS) subject presenting with functional decline of organ systems associated with accelerated aging due to over-production of $H_2S$ that comprises administering a pharmaceutical composition containing a concentration of about 0.1 to about 10 mg/kg of poly (ethylene glycol)-substituted oxidized carbon nanoparticles (PEG-OCNPs) dissolved or dispersed in a physiologically acceptable diluent to the subject, wherein said PEG substituent has average molecular weight of about 2000 to about 10,000 Da, and said PEG-OCNPs contain an average of about 3 to about 12 PEG substituents per particle.

18. The method according to claim 17, wherein said PEG-OCNPs are present at a concentration of about 0.5 to about 6 mg/kg.

19. The method according to claim 17, wherein said PEG substituent has average molecular weight of about 5000 Da.

20. The method according to claim 17, wherein said PEG-OCNPs contain an average of about 5 to about 10 PEG substituents per particle.

21. The method according to claim 17, wherein said administration is provided to a patient having an elevated level of $H_2S$.

22. The method according to claim 17, wherein said administration is repeated.

23. The method according to claim 17, wherein the pharmaceutical composition further comprises lipoic acid, dihydrolipoic acid, or a combination thereof.

24. The method according to claim 23, wherein said lipoic acid is present at about 0.5 to about 3 mM.

* * * * *